(12) United States Patent
Guerrero Martinez et al.

(10) Patent No.: US 9,267,151 B2
(45) Date of Patent: Feb. 23, 2016

(54) STXBP1 OVEREXPRESSING MOUSE AND ITS USES IN SCREENING OF TREATMENTS FOR NEUROPSYCHIATRIC ILLNESS

(75) Inventors: Maria Jose Guerrero Martinez, Vizcaya (ES); Laureano Simon Buela, Vizcaya (ES); Marcel Ferrer-Alcon, Vizcaya (ES); Antonio Martinez Martinez, Vizcaya (ES); Jose Javier Meana, Bizkaia (ES); Luis Felipe Callado, Bizkaia (ES); Leyre Uriguen, Bizkaia (ES)

(73) Assignees: Brainco Biopharma, S.L., Derio (ES); Universidad del Pais Vasco/Euskal Herriko Unibertsitatea, Leioa (ES)

( * ) Notice: Subject to any disclaimer, the term of this patent is extended or adjusted under 35 U.S.C. 154(b) by 1337 days.

(21) Appl. No.: 13/059,938

(22) PCT Filed: Aug. 18, 2009

(86) PCT No.: PCT/EP2009/060674
§ 371 (c)(1),
(2), (4) Date: Jun. 14, 2011

(87) PCT Pub. No.: WO2010/020642
PCT Pub. Date: Feb. 25, 2010

(65) Prior Publication Data
US 2011/0268747 A1 Nov. 3, 2011

Related U.S. Application Data

(60) Provisional application No. 61/090,607, filed on Aug. 20, 2008.

(51) Int. Cl.
*A01K 67/027* (2006.01)
*G01N 33/00* (2006.01)
*C12N 15/85* (2006.01)

(52) U.S. Cl.
CPC .......... *C12N 15/8509* (2013.01); *A01K 67/027* (2013.01); *A01K 2217/052* (2013.01); *A01K 2227/105* (2013.01); *A01K 2267/03* (2013.01)

(58) Field of Classification Search
USPC ............................................. 800/3, 8, 18, 21
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 6,358,698 B1 * | 3/2002 | Weiner et al. | 435/7.21 |
| 7,947,807 B2 * | 5/2011 | Kobilka et al. | 530/350 |
| 2002/0187163 A1 * | 12/2002 | Johnson et al. | 424/205.1 |
| 2005/0227233 A1 * | 10/2005 | Buxton et al. | 435/6 |
| 2010/0235933 A1 * | 9/2010 | Meitinger et al. | 800/13 |

FOREIGN PATENT DOCUMENTS

EP WO 2005/023858 * 3/2005
WO WO/2009/084472 7/2009

OTHER PUBLICATIONS

Pevsner, PANS, Feb. 1994, vol. 91, p. 1445-1449.*
Gengyo-Ando (J. Neurosci., Nov. 1, 1996, vol. 16, No. 21, p. 6695-6702).*
Verhage (Science, Feb. 4, 2000, vol. 287, p. 864-869).*
Yang (Neuron, Nov. 2000, vol. 28, p. 375-383).*
Toonen (PNAS, Nov. 28, 2006, vol. 103, No. 48, p. 18332-18337).*
Hamdan (Ann. Neurol., 2009, vol. 65, p. 748-753).*
Saitsu (Nature Genetics, Jun. 2008, vol. 40, No. 6, p. 782-788).*
Dallman (Physiology & Behavior, 2013, p. 97-105).*
Wall (1996, Theriogenology, vol. 45, p. 57-68).*
Ebert (1988, Mol. Endocrinology, vol. 2, pp. 277-283).*
Mullins (1990, Nature, vol. 344, p. 541-544).*
Hammer (1990, Cell, vol. 63, p. 1099-1112).*
Mullins, 1989, EMBO, vol. 8, p. 4065-4072.*
Taurog, 1988, J. Immunol., vol. 141, p. 4020-4023.*
Cowan (Xenotransplantation, 2003, vol. 10, p. 223-231).*
Low (Neuron, May 3, 2007, 54, p. 348-349).*
Paylor (Psychopharmacology, 1997, vol. 32, p. 169-180).*
Brody, 1004, Mol. Psychiatry, 2004, vol. 9, p. 35-41.*
Grauer, Psycholpharm. 1999, vol. 141, p. 405-412.*
Harrison, 2003, Mol. Cell. Neurosci., vol. 24, p. 1170-1179.*
Belzung, Behavioural Brain Res. 2001, vol. 125, p. 141-149.*
Arguello and Gogos, "Modeling Madness in Mice: One Piece at a Time," *Neuron*, vol. 52, pp. 179-196, 2006.
Behan et al., "Proteomic analysis of membrane microdomain-associated proteins in the dorsolateral prefrontal cortex in schizophrenia and bipolar disorder reveals alterations in LAMP, STXBP1 and BASP1 protein expression," *Molecular Psychiatry* vol. 14, pp. 601-613, 2009.
Behan, "Proteomic Analysis of Membrane Microdomain-Associated Proteins in the Dorsolateral Prefrontal Cortex in Schizophrenia and Bipolar Disorder Reveals Alterations in LAMP, STXBP1 and B," *Schizophrenia Research* 102/1-3, Supplement 2, p. 219, 2008.
Bhardwaj et al., "Behavorial characterization of dysbindin-1 deficient sandy mice," *Behavioural Brain Research*, vol. 197, pp. 435-441, 2009.
Bracher and Weissenhorn, "Crystal Structures of Neuronal Squid Sec1 Implicate Inter-domain Hinge Movement in the Release of t-SNAREs," *J. Mol. Biol.* vol. 306, pp. 7-13, 2001.
Castillo et al., "Deficits in Syntaxin 1 Phosphorylation in Schizophrenia Prefrontal Cortex," *Biol. Psychiatry*, vol. 67, pp. 208-216, 2010.
Crawley, "Emotional Behaviors: Animal Models of Psychiatric Diseases," In *What's Wrong with My Mouse? Behavioural Phenotyping of Transgenic and Knockout Mice*, Chapter 10, pp. 179-206, Wiley-Liss, 2000.

(Continued)

Primary Examiner — Michael Wilson
(74) Attorney, Agent, or Firm — Klarquist Sparkman, LLP

(57) ABSTRACT

A non-human transgenic animal having a polynucleotide encoding an STXBP1 polypeptide, which polynucleotide is operably linked to a promoter, wherein said transgenic animal has greater than wild-type expression of the STXBP1 polypeptide in at least one brain region, as well as related vectors, methods of producing transgenic animals, in vitro and in vivo screening methods for potential therapeutic agents, and methods for treating and diagnosing neuropsychiatric illness are disclosed.

10 Claims, 19 Drawing Sheets

(56) References Cited

OTHER PUBLICATIONS

Dawe and Ratty, "The *chakragati* mouse: A mouse model for rapid in vivo screening of antipsychotic drug candidates," *Biotechnology Journal*, vol. 2, pp. 1344-1352, 2007.

Ellenbroek and Cools, "Animal models for the negative symptoms of schizophrenia," *Behavioural Pharmacology*, vol. 11, pp. 223-233, 2000.

Fatemi et al., "Altered levels of the synaptosomal associated protein SNAP-25 in hippocampus of subjects with mood disorders and schizophrenia," *NeuroReport*, vol. 12, pp. 3257-3262, 2001.

Gengyo-Ando et al., "A Murine Neural Specific Homolog Corrects Cholinergic Defects in *Caenorhabditis elegans unc-18* Mutants," *J. Neurosci*. vol. 16, pp. 6695-6702, 1996.

Geyer and Moghaddam, "Animal Models Relevant to Schizophrenia Disorders," In *Neuropharmapsychology: The Fifth Generation of Progress*, Eds. Davis et al., Chapter 50, pp. 689-701, Lippincott Williams & Wilkins, 2002.

Gray et al., "*N*-Ethylmaleimide sensitive factor in the cortex of subjects with schizophrenia and bipolar I disorder," *Neuroscience Letters*, vol. 391, pp. 112-115, 2006.

Halim et al., "Presynaptic proteins in the prefrontal cortex of patients with schizophrenia and rats with abnormal prefrontal development," *Molecular Psychiatry*, vol. 8, pp. 797-810, 2003.

Hattori et al., "Behavioral abnormalities and dopamine reductions in *sdy* mutant mice with a deletion in *Dtnbp1*, a susceptibility gene for schizophrenia," *Biochemical and Biophysical Research Communications*, vol. 373, pp. 298-302, 2008.

Hikita et al., "Proteomic analysis reveals novel binding partners of dysbindin, a schizophrenia-related protein," *Journal of Neurochemistry*, vol. 110, pp. 1567-1574, 2009.

Honer et al., "Abnormalities of SNARE Mechanism Proteins in Anterior Frontal Cortex in Severe Mental Illness," *Cerebral Cortex*, vol. 12, pp. 349-356, 2002.

Imai et al., "A quantitative study on the expression of synapsin II and N-ethylmaleimide-sensitive fusion protein in schizophrenic patients," *Neuroscience Letters*, vol. 305, pp. 185-188, 2001.

Koike et al., "Behavioral abnormality and pharmacologic response in social isolation-reared mice," *Behavioural Brain Research*, vol. 202, pp. 114-121, 2009.

Low and Hardy, "What Is a Schizophrenic Mouse?" *Neuron* vol. 54, pp. 348-349, 2007.

Ma et al., "The Transcription Factor Regulatory Factor X1 Increases the Expression of Neuronal Glutamate Transporter Type 3," *J. Biol. Chem*. vol. 281, pp. 21250-21255, 2006.

McLean et al., "$D_1$-like receptor activation improves PCP-induced cognitive deficits in animal models: Implications for mechanisms of improved cognitive function in schizophrenia," *European Neuropsychopharmacology*, vol. 19, pp. 440-450, 2009.

Mukaetova-Ladinska et al., "Loss of synaptic but not cytoskeletal proteins in the cerebellum of chronic schizophrenics," *Neuroscience Letters*, vol. 317, pp. 161-165, 2002.

Novikova et al., "Identification of protein biomarkers for schizophrenia and bipolar disorder in the postmortem prefrontal cortex using SELDI-TOF-MS ProteinChip profiling combined with MALDI-TOF-PSD-MS analysis," *Neurobiology of Disease*, vol. 23, pp. 61-76, 2006.

Powell and Miyakawa, "Schizophrenia-Relevant Behavioral Testing in Rodent Models: A Uniquely Human Disorder?" *Biol. Psychiatry*, vol. 59, pp. 1198-1207, 2006.

Powell et al., "Prepulse inhibition and genetic mouse models of schizophrenia," *Behavioural Brain Research*, vol. 204, pp. 282-294, 2009.

Rodgers and Cole, "Anxiolytic-like effect of (*S*)-WAY 100135, a $5\text{-HT}_{1A}$ receptor antagonist, in the murine elevated plus-maze test," *European Journal of Pharmacology*, vol. 261, pp. 321-325, 1994.

Rössler et al., "Size of burden of schizophrenia and psychotic disorders," *European Neuropsychopharmacology*, vol. 15, pp. 399-409, 2005.

Söllner et al., "A Protein Assembly-Disassembly Pathway In Vitro That May Correspond to Sequential Steps of Synaptic Vesicle Docking, Activation, and Fusion," *Cell*, vol. 75, pp. 409-418, 1993.

Söllner et al., "SNAP receptors implicated in vesicle targeting and fusion," *Nature*, vol. 362, pp. 318-324, 1993.

Spurlin et al., "Insulin Resistance in Tetracycline-Repressible Munc18c Transgenic Mice," *Diabetes*, vol. 52, pp. 1910-1917, 2003.

Srivastava et al., "Age and gender related differences in human parotid gland gene expression," *Archives of Oral Biology*, vol. 53, pp. 1058-1070, 2008.

Swanson et al., "Identification and Characterization of the Human Ortholog of Rat STXBP1, a Protein Implicated in Vesicle Trafficking and Neurotransmitter Release," *Genomics*, vol. 48, pp. 373-376, 1998.

Takao et al., "Impact of brain-behavior phenotypying of genetically-engineered mice on research of neuropsychiatric disorders," *Neuroscience Research*, vol. 58, pp. 124-132, 2007.

Thompson et al., "Elevated Cerebrospinal Fluid SNAP-25 in Schizophrenia," *Biol. Psychiatry*, vol. 53, pp. 1132-1137, 2003.

Vercauteren et al., "An organelle proteomic method to study neurotransmission-related proteins, applied to a neurodevelopmental model of schizophrenia," *Proteomics*, vol. 7, pp. 3569-3579, 2007.

Verhage et al., "Synaptic Assembly of the Brain in the Absence of Neurotransmitter Secretion," *Science*, vol. 287, pp. 864-869, 2000.

Voets et al., "Munc18-1 Promotes Large Dense-Core Vesicle Docking," *Neuron*, vol. 31, pp. 581-591, 2001.

Weinberger, "Genetic Mechanisms of Psychosis: In Vivo and Postmortem Genomics," *Clinical Therapeutics*, vol. 27, pp. S8-S15, 2005.

Young et al., "SNAP-25 Deficit and Hippocampal Connectivity in Schizophrenia," *Cerebral Cortex*, vol. 8, pp. 261-268, 1998.

\* cited by examiner

Figure 10A

```
   1 gcggggcgcg cggcccgggg gaggcgacgg tgtcgcggga ggagcatcgg agcccgaaga
  61 ctcgaagaac gccatggccc ccattggcct caaggcggtg gtcggagaga agatcatgca
 121 tgatgtgatc aagaaggtga agaagaaggg cgagtggaag gtgctggtgg tggaccagtt
 181 aagcatgagg atgctgtcct cctgctgcaa gatgacagac atcatgaccg agggcatcac
 241 aattgtggag gatatcaaca agcgccgaga gccactcccc agcctggagg ccgtgtacct
 301 catcacccca tctgagaagt ctgtccactc tctgatcagt gattttaagg acccgccgac
 361 tgctaaatat cgggctgcgc atgtgttctt cacagactcg tgtccagatg ccctatttaa
 421 cgagctggta aaatcccgag cagccaaagt catcaagacg ctgacggaaa tcaacattgc
 481 gttttctcccc tatgagtccc aggtgtattc cctggactcc gctgactctt ccaaagcttt
 541 ctacagccct cacaaggcgc agatgaagaa tccgatactg aacgcctgg cagagcagat
 601 cgcaaccctg tgtgccaccc tgaaggagta tccagctgtg cggtatcggg gggagtacaa
 661 ggacaatgcc ttgctggctc agctgatcca ggacaagctg gatgcctata agccgacga
 721 tccaacaatg ggggagggtc ccgacaaggc acggtcccag ctcctgatcc tggatcgtgg
 781 ctttgacccc agctcccctg tgctccatga actgacattc caggctatga gttatgacct
 841 gctgcctatc gaaaatgatg tttacaagta tgagaccagc ggcattggag aggcgcgggt
 901 gaaggaggtg ctactggatg aggacgatga cctgtggatt gcgctgcgac acaagcacat
 961 cgcagaggtg tcccaggaag tcacccggtc tctgaaggac ttttcctcta gcaagaggat
1021 gaacactggc gagaagacca ccatgcggga cctgtcccag atgctgaaga aaatgcccca
1081 gtaccagaag gagctcagca gtattcgac tcacctgcac cttgctgaag actgcatgaa
1141 gcattaccaa ggcactgtag acaaactctg ccgcgtggag caggacctgg caatgggcac
1201 agatgctgag ggggaaaaaa tcaaggaccc catgagagcc attgtcccca tcctgctgga
1261 tgcgaacgtc agcacttacg acaaaatccg tatcatcctt ctctacatct tcctgaagaa
1321 cggtatcact gaggagaacc taaacaaact catccagcac gctcagatac ccccagagga
1381 cagcgagatc atcaccaaca tggctcacct cggcgtgccc atcgtcacgg attccacact
1441 acgccgccga agcaaaccgg agcggaagga gcgtatcagt gagcagacct accagctctc
1501 acgatggacc ccgatcatta agacattat ggaggacact atcgaagaca agctggatac
1561 aaagcactac ccatacatct ctacccgctc gtccgcgtcc ttcagcacca ctgctgtgag
1621 tgcccgctat ggacattggc acaagaataa ggcccccggg gagtaccgca gcggtccccg
1681 cctcattatt ttcatccttg ggggtgtgag cctgaatgag atgcgctgtg cttacgaagt
1741 gacccaggcc aacggcaagt gggaagtgct gataggttct actcacattc tcactcccac
1801 caaattcctc atggacctga gacaccccga cttcagggag tcctctaggg tatcttttga
1861 ggatcaggct ccaacaatgg agtgagagcc aaagagacaa agatccacgc acattctcac
1921 cccacagaaa ctgctggaca cgctgaagaa gctgaataaa acagatgaag aaataagcag
1981 ttaaaaaata agctgccccc caaaacccg gctcccttcc caaaatgctc tgcagctccc
2041 ccgtgcgcca cctcggttac tctgctgcct ccccagccct gcacgccctg gccaccccgt
2101 tgccgtgctg agttcttctc ctgtgcgatg acaccccatc ttgtcctctg aaaagcaaga
2161 gagtaatgtg ttgtttttta aaaatgagca tcttctgtat gtatcccaca gtaagttcac
2221 atgcaagctc cacactgcag aagcgtcaga actccggacc gagtgaattc tcccttattt
2281 atgaccccgt gacctgtata tagccctgtc ccgcgtgtgc acattgcttg aatatggaaa
2341 ggtagatgtg tgggtgtctc tccaagcttg gttggattca tttctgtcct tgttggtgtt
2401 tgttccccgg ataggacatg ctgagggagt gatgttctcg ctagcccctg ctcgctccct
2461 gttctcagcg atgagcagac acctctggag gctggcgtgg aacgagcctc ctctttgcac
2521 ctatggggga ggcttagggt gtccacagga agccagtctg agtgccggcc agtgtggtct
2581 ccagagcctg gcactgcttt ccctgatctg tgtccatact gttgtaacaa gttaagccct
2641 tcaggctaaa tcagcctgcc tagtgccctc ggagcctcca gagttaggtc tgaccagccc
2701 cctgcttgaa cacagtttgg atagaggcca agggtcaggg gtgggctgga agctgtgagt
2761 ttggcactct ggtcaagggt gctttgctgt aggagctagg cctgaagaat ggggcccctg
2821 ctgcttagtc agagtcccct cagtttaaga tacttcatca atcttaagtt tgtgtagtgt
2881 acagtcatgt gtcattgtgg ttgtatgaaa aggatcattt tattctttgt attagtcatc
2941 actgtataaa acatagctag ctataaagca gaaattccag aagccgatgc tggaaggatg
3001 gtctccaccc tcaggacgca gcagcccct gagcatgctg ctcaccctgc tgctgtagtc
3061 gtgaaacaaa gacagtggaa gtcacaaaaa tgtccccagc ccagtccccg ccctccctc
3121 ccgcagattt gtacgtatta ctgtgtctcg tgctgtcttc gcaaacgtgg tgtacgcctg
3181 ccgcaggtgt cctgtgccct tctccctccc tgactctaga gtctctcttc tccttagttc
3241 tcaggcctct cccctgctcc tctccagtga acctttccc ttaggactga accacactag
3301 caccggttga tttcttctgt agcgcttctc ccatcccttc ctccggtcaa gcaatgctca
3361 tgcttcagga tcttgtttgt cgaacatgtg gggtttcctt tatgttattt atataaataa
3421 tttctcaaat ggatatttaa aaaaagcta gtctgtcttg aacttgtta acttgaaact
3481 cttgaatctc agtgtttaaa gtatggaagc acaaccgtgt accgctctgt accgtcctgt
```

Figure 10B

```
3541 actgcagcat ttgagtctaa taaagacgtc agctctcaaa aaaaaaaaaa aaaaaaaaaa
3601 aaaaaaaaaa aaaaaa
```

Figure 11

```
MAPIGLKAVVGEKIMHDVIKKVKKKGEWKVLVVDQLSMRMLSSCCKMTDIMTEGITIVEDINKRREPLPSLE
AVYLITPSEKSVHSLISDFKDPPTAKYRAAHVFFTDSCPDALFNELVKSRAAKVIKTLTEINIAFLPYESQV
YSLDSADSFQSFYSPHKAQMKNPILERLAEQIATLCATLKEYPAVRYRGEYKDNALLAQLIQDKLDAYKADD
PTMGEGPDKARSQLLILDRGFDPSSPVLHELTFQAMSYDLLPIENDVYKYETSGIGEARVKEVLLDEDDDLW
IALRHKHIAEVSQEVTRSLKDFSSSKRMNTGEKTTMRDLSQMLKKMPQYQKELSKYSTHLHLAEDCMKHYQG
TVDKLCRVEQDLAMGTDAEGEKIKDPMRAIVPILLDANVSTYDKIRIILLYIFLKNGITEENLNKLIQHAQI
PPEDSEIITNMAHLGVPIVTDSTLRRRSKPERKERISEQTYQLSRWTPIIKDIMEDTIEDKLDTKHYPYIST
RSSASFSTTAVSARYGHWHKNKAPGEYRSGPRLIIFILGGVSLNEMRCAYEVTQANGKWEVLIGSTHILTPT
KFLMDLRHPDFRESSRVSFEDQAPTME
```

Figure 12A

```
   1 ctgacgcgcg gctgcggggc ggagagctgc ggctggccca gcgcgcccac ctgaggaggc
  61 ggcggggtcc gcaggcgtcg cgggacgagg agatcggagc cgggagactc gcgcagcgcc
 121 atggccccca ttggcctcaa agctgttgtc ggagagaaga ttatgcatga tgtgataaag
 181 aaggtcaaga agaaggggga atggaaggtg ctggtggtgg atcagttaag catgaggatg
 241 ctgtcctcct gctgcaagat gacagacatc atgaccgagg cataacgat tgtggaagat
 301 atcaataagc gcagagagcc gctccccagc ctggaggctg tgtatctcat cactccatcc
 361 gagaagtccg tccactctct catcagtgac tttaaggacc cgccgactgc taaataccgg
 421 gctgcacacg tcttcttcac tgactcttgt ccagatgccc tgtttaatga actggtaaaa
 481 tcccgagcag ccaaagtcat caaaactctg acggaaatca atattgcatt tctcccgtat
 541 gaatcccagg tctattcctt ggactctgct gactcttcc aaagcttcta cagtccccac
 601 aaggctcaga tgaagaatcc tatactggag cgcctggcag agcagatcgc gacccttgt
 661 gccaccctga aggagtaccc ggctgtgcgg tatcggggg aatacaagga caatgccctg
 721 ctggctcagc taatccagga caagctcgat gcctataaag ctgatgatcc aacaatgggg
 781 gagggcccag acaaggcacg ctcccagctc ctgatcctgg atcgaggctt tgaccccagc
 841 tcccctgtgc ccatgaatt gactttcag gctatgagtt atgatctgct gcctatcgaa
 901 aatgatgtat acaagtatga accagcggc atcggggagg cacgggtgaa ggaggtgctc
 961 ctggacgagg acgacgacct gtggatagca ctgcgccaca agcacatcgc agaggtgtcc
1021 caggaagtca cccggtctct gaaagatttt tcttctagca agagaatgaa tactggagag
1081 aagaccacca tgcgggacct gtcccagatg ctgaagaaga tgcctcagta ccagaaagag
1141 ctcagcaagt actccaccca cctgcacctt gctgaggact gtatgaagca ttaccaaggc
1201 accgtagaca aactctgccg agtggagcag gacctggcca tgggcacaga tgctgaggga
1261 gagaagatca aggacctat gcgagccatc gtccccattc tgctggatgc caatgtcagc
1321 acttatgaca aaatccgcat catccttctc tacatctttt tgaagaatgg catcacggag
1381 gaaaacctga caaactgat ccagcacgcc cagataccc cggaggatag tgagatcatc
1441 accaacatgg ctcacctcgg cgtgcccatc gtcaccgatt ccacgctgcg tcgccggagc
1501 aagccggagc ggaaggaacg catcagcgag cagacctacc agctctcacg gtggactccg
1561 attatcaagg acatcatgga ggacactatt gaggacaaac ttgacaccaa acactaccct
1621 tatatctcta cccgttcctc tgcctccttc agcaccaccg ccgtcagcgc ccgctatggg
1681 cactggcata agaacaaggc cccaggcgag taccgcagtg gccccgcct catcattttc
1741 atccttgggg gtgtgagcct gaatgagatg cgctgcgcct acgaggtgac ccaggccaac
1801 ggaaagtggg aggtgctgat aggttctact cacattctta ctcccaccaa atttctcatg
1861 gacctgagac accccgactt caggggagtcc tctagggtat cttttgagga tcaggctcca
1921 acaatggagt gagagccaaa gaaacaaaga tccacacaca tcctcacccc acagaaactg
1981 ctggacacac tgaagaaact gaataaaaca gatgaagaaa taagcagtta aaaaaataag
2041 tcgcccctcc aaaacacgcc cccatcccac agcgctccgc agcttccac caccgcccgc
2101 ctcagttcct ttgcgtctgt tgcctcccca gccctgcacg ccctggctgg cactgttgcc
2161 gctgcattct cgtgttcagt gatgccctct tcttgtttga acaaaagaa aataatgcat
2221 tgtgtttttt aaaagagta tcttatacat gtatcctaaa aagagaagct catgtgcaat
2281 tggtgcacag caggagaaat ttctggactg ttaggatgaa tggacgcctt ctccccgtta
2341 tttaagattt gtgaccttgt acataaccct gggtgacgtg cacattgctt gggtatggaa
```

Figure 12B

```
2401 cggtagaaat ttgggtgttt ttaaaacctt gtttggggtt gttcctgtcc ttgttgagaa
2461 tcatagagat gtctgtgttc ttggagtatt tcacactgag gactaatctg ctatcttcat
2521 tccagtccct acccctcagt gcctgctctc atccaaataa cctgggaggt gacaatcagg
2581 atatctcagg aggtccaagg tggaacagac ctctttgcct ttcccagcgt ctcataccc
2641 cggtagtgca gctgtgggtg gaggctgggg tgtctgcacg aagtcaggcc agcgtcctcc
2701 tccacagcct gtcactgccc cctccccagc ctgtgtccac agtgctgtga tcccgaggga
2761 agtcctccag tctaagtcac agtgccctga caggtgagaa gcaaactccc gctggaagcc
2821 tccatctctt tggaaaaaca gttagtctgg agcctgtggc ccaggcccctt ctgtccccag
2881 gcatcatccc aacagctcat tttccctagt ccgccttcgt tcaagggtca ggaatggacc
2941 agaacagatg ggttctggag gccctgaac agagggctat ggctgtggag aaggttcttg
3001 gcccgttgga ctcacacaga ccctgtaccc tctcggcaag catcttcagt cagattatcc
3061 tcagtttcag atacttcata ataccttgtg ttgtgtgggg tcatacatca tcgtgtttgt
3121 aagagaagat ggtcatttta ttctctgtat aaaacttagc tctaaagcag aaactaaagc
3181 agcaaatgca ggaaggctgt ctcgccatcc tcaagactca gcagctctca ttctccagtg
3241 gtgagcacac catttgtgct gctgctgttg tcgtgaaata taataacagt ggaagtcaca
3301 aaaatgtccc ctgcccagcc ccctcgccgc ccttgacctc ctgcaggcca tgtgtgtatt
3361 acttgtctag tgatgtcctc tcaaagtgct gtacgcgagc tcggcgccac ctccgcctcc
3421 ctttcagagc ctgctccccg ccctctctgc tcgctgcatt gtggtgttct cttctcaagg
3481 ctttgaaatc tccccttgca ctgagattag tcgtcagatc tctccccgtc tccctcccaa
3541 cttatacgac ctgatttcct taggacggaa ccgcaggcac ctgcgccggg cgtcttactc
3601 ccgctgcttg ttctgtcccc tccctcggac caaacagtgc tcatgcttca ggaccttgtt
3661 tgtcgaagat gttggtttcc ctttctctgt tatttatata aaataatttt atcaaaagga
3721 tattttaaaa aagctagtct gtcttgaaac ttgtttacct taaaattatc agaatctcag
3781 tgtttgaaag tactgaagca caaacatata tcatctctgt accattctgt actaaagcac
3841 ttgagtctaa taaataaaga aatcagcacc ccttcccggt gtccagggg aaaaaaaaa
```

Figure 13

```
Uniprot P61764 (STXBP1_HUMAN)
         10         20         30         40         50         60
MAPIGLKAVV GEKIMHDVIK KVKKKGEWKV LVVDQLSMRM LSSCCKMTDI MTEGITIVED 70         80         90        100        110        120
INKRREPLPS LEAVYLITPS EKSVHSLISD FKDPPTAKYR AAHVFFTDSC PDALFNELVK 130        140        150        160        170        180
SRAAKVIKTL TEINIAFLPY ESQVYSLDSA DSFQSFYSPH KAQMKNPILE RLAEQIATLC 190        200        210        220        230        240
ATLKEYPAVR YRGEYKDNAL LAQLIQDKLD AYKADDPTMG EGPDKARSQL LILDRGFDPS 250        260        270        280        290        300
SPVLHELTFQ AMSYDLLPIE NDVYKYETSG IGEARVKEVL LDEDDDLWIA LRHKHIAEVS 310        320        330        340        350        360
QEVTRSLKDF SSSKRMNTGE KTTMRDLSQM LKKMPQYQKE LSKYSTHLHL AEDCMKHYQG 370        380        390        400        410        420
TVDKLCRVEQ DLAMGTDAEG EKIKDPMRAI VPILLDANVS TYDKIRIILL YIFLKNGITE 430        440        450        460        470        480
ENLNKLIQHA QIPPEDSEII TNMAHLGVPI VTDSTLRRRS KPERKERISE QTYQLSRWTP 490        500        510        520        530        540
IIKDIMEDTI EDKLDTKHYP YISTRSSASF STTAVSARYG HWHKNKAPGE YRSGPRLIIF 550        560        570        580        590
ILGGVSLNEM RCAYEVTQAN GKWEVLIGST HILTPQKLLD TLKKLNKTDE EISS
```

Figure 14A

```
   1 gcgctgacag cggccggtgc gcgttgtctc cactgtgccc tgcatcccgc atctcgcatc
  61 ggccaggcta cccgactcat cgcaaacgtc agtgctcacc atggggaagc ccacgagctc
 121 gggatgtgac tggcgccgct tcctacggaa tcactggctg ctgctctcca ccgtggccgc
 181 cgtggtacta ggaattgtct taggagtcgt ggttcgagga cacagtgagc tctcaaatct
 241 ggataaattc tactttgctt ttcctgggga aattctgatg aggatgctga agctggtcat
 301 tttgccgctg atcgtatcca gcatgatcac aggtgtcgct gcactggatt ccaatgtgtc
 361 tgggaagatt ggtctgcgcg ctgtagtata ttatttctcc accaccgtca ttgctgtaat
 421 cctaggtatt gtgttagttg tgagtatcaa gcctggtgtc actcagaaag tgaatgacat
 481 caacaggacg ggtaaaaccc ctgaagtcag caccatggat gccatgttgg acctgatcag
 541 gaacatgttc cctgagaatc tggtccaagc ctgttttcag cagtacaaaa ccaagcggga
 601 agaggtgaag cctgtgggcg atcctggggg gaacgcaacg gaggtgtctg tcaccacagc
 661 catgacaaca atgtctgaga acaagacaaa ggaatacaag atcgtgggcc tgtactcaga
 721 cggcatcaat gtcctgggct tgattatctt ctgcctcgtc tttggccttg tcattgggaa
 781 aatgggagaa aaggggcaga ttctggtgga cttcttcaat gccttgagtg acgccaccat
 841 gaaaatcgtc cagatcatca tgtgctacat gccgattggc atttgttcc taattgctgg
 901 gaagatcata gaagttgaag actgggaaat attccgcaag ctgggccttt acatggccac
 961 tgtcctgagc gggcttgcaa tccactccct catagttctg cccctgctct atttcatagt
1021 tgtgcggaag aaccctttcc gctttgcctt gggtatggcg caggctctcc tgacagctct
1081 catgatctcg tccagttcgg caaccctgcc agttacattc cgctgtgcgg aagaaaagaa
1141 ccaggtagac aagaggatca cgagatttgt gctgcctgtt ggtgccacca tcaacatgga
1201 cggcactgcg ctctacgaag ctgtggcagc cgtgtttatt gcgcaactga atggcttgga
1261 cctaagcatt gggcagatcg tcaccatcag cattacagcc accgctgcca gcattggagc
1321 tgctggggtg ccccaggctg gcctggtgac catggtgatc gtgctgagtg ctgtggggct
1381 gcctgccgag gacgtcaccc tgatcattgc tgttgactgg ctcctggacc ggttcaggac
1441 catggtgaac gtcctgggtg atgcgtttgg gacggcatc gtagagaagc tctcgaagaa
1501 ggagctggag cagatggatg tttcgtctga agtcaacatc gtgaacccct tgccctgga
1561 acccacaacc ctcgataacg aagactcaga taccaagaag tcttatgtca atgggggctt
1621 cgcggtagac aaatctgaca ccatctcgtt cactcagacc tcacagttct agatgcctga
1681 cctcagattg aggcctggga ttgtgaaggg cgtctccaca ggagccatct cctagcaaac
1741 tccgacatta aggaacgaga aggacactaa gagtcaactg tacatttagt ttgataaaca
1801 gacctccaga ttattttcta tatttgactt tatagccttg gttctctggg tttagggatt
1861 tggggtgaga tgaactgaaa ggaaattaag aaagttgtgt tatctggatt ttctaattct
1921 atacaacaga gtttggaagt atatgaagta gtaactgtta ggattaggtc atagatatgg
1981 aagagaaatt ggtttctcat gcatagacca gtgtttgggg tttttaaaca atattattgg
2041 ctacaaattt ttactcaggc tttctattgg caggacttcc tttgcctttt tactttata
2101 gattataatg catctcaaaa gccctaccca gttaatgtgc caaattttcc attttgacct
2161 catctccagc cactctcaaa ctaccctggg gcgggggag caaaaaagat cagcatagtt
2221 ctgcaataac agtttaaaga tagttgtggg gtttagggga agggaaggg tttttttatt
2281 caatgtactg tattgagaca ctggtagctg acagccagtg ttcggtatag aactatatgt
2341 atatgtgtgt atatttatta ttttcatgta atttgcaaga cagagatcag taatgaacta
2401 tcaatgtgaa atacgcagct ttccttgtac ttgaatcaaa acgatagctc cagcctaggt
2461 gtgagctcac cagaacactg tcaggcactc tgggatgaga aatcaagttg ctggcttact
2521 gtgattcaag ccctaaagca gaaacatatt atggtgaaac tctaagatga cacagccatt
2581 cacgtacaac atctagggtc aggctccgg gaggggagg ctccctgcga gcatggaata
2641 agtacattta caaaggcact gtagaggcag gaagtgctcc catagcaaca aaaggcttcg
2701 atcttcaagt agacttcaag acccacttca caaggctgtc acttttctgt tcttggtttt
2761 ctctgcctgc gcccccacc cccagggcca aaccagcagt gacaagccac tgctgtttca
2821 aaacggggtg gcctaaattg aataagcctc attgcaaggt gaccaagcta tccttatact
2881 gtcgtctttt tattttatct tctggttttt ttattttta gttttgaga cagcgcctct
2941 ctacatagcc ctggatatcc tggaactcac tatgtagact agactggcct caaactcaca
3001 gagatcctcc tgcctctgcc tctttagtgc tggcctgaaa ggtaggtacc accatgccca
3061 gctctacact gtattttac agaagaaaag ccaggccata agcgactggt accagcggtt
3121 cagggacaat acttcagtcc ttccctggag aggattgttc tgggaatctc agccttgtgg
3181 cttagaatcc tctgcctgtc tttctcctgc taattcccga agatggctta taaagtcta
3241 cacttctgtc ctcatcctgt aaataaaact caacaaaaac ttgttcttaa cttggagaca
3301 ggttcataac agccgttctt ctgtagtgcc cttaagtcat cttaaacccg tgcttttata
3361 tttaagaagc cagaaatcgt gccaaagata gcaggaaggt aaccgaatgc tcagagttgg
3421 ccacgcccac ctgaaagcta ccgactgacc gtcacggtga cccttgactc cgaactttga
3481 agtacaaata tctgtattct ttataggaag taaatctaaa tctaaatgag gttgaatgga
```

Figure 14B

```
3541 tattttattt aggagtggat ggttctgtcc ccttatcagg tggttctcct tagtggcagt
3601 gaattggcag agccgttcac aagatcattg gggtcatctt gtaaccagcc acttcacaca
3661 ctgtgctgtt aactcaagat gatatgttcc acttccttct caataaacat ctcccccact
3721 ctttctcccc ttaaaaaaaa aaaaaaaaaa aaaa
```

Figure 15A

```
   1 tagtccaacc agagacagag cacactcacc attttcagag agagggaagg ggctcaacct
  61 atgaagagaa acaaaacaa acaatgaca aacacagtcc tctttggatt cttctccctt
 121 tttatttgta gtaatgaggg atgaacctac agctcggtgc atactagaaa aaaacctacc
 181 ctggagctat atccataccc attttctttt tgttttgaaa cagagtctca ctaagttatc
 241 caaacagttc tgaatttgca atcctcctgc ctctatctgc caaggagctg ggggatagaa
 301 acttgcttgc accgctgtgt tgcgctgtct ttggaggttt aatcaaataa ataaaaatat
 361 atagccagct aatgtgtgtt gagtatggat tgcctgtgat ggaggaataa gcacgctact
 421 atttcattct gacagccttt attcctgcag ttctgagaag ttggaaggag aaagttcact
 481 gaagttgtca atgctcacag atttctctaa caggcgctgg gctctgtgtt ctctccccac
 541 caaggcttat ttacccacac tgatgcctta agcttcggga attcctccac gccctctgat
 601 ttcctgtaac tgaatagagg cctggcaagg ctctatttag cactcacctc aaggtctcag
 661 agttgagtat ttcctgcact gtaggccctt agaagacaga gcaaggcaag catttcccct
 721 ttgtgactcc ccactgtgcc ttaccagcat taggaaggcc ttagaatacc tgctagcagg
 781 gtactaagca gtctcaacat ttttctccca ttttatctat tcagaggcaa ccacaatgat
 841 caatgacaac aggacctgag atcaacagca gcaggtgttt attttaaaag tatagaaaac
 901 aggttaaaac actgtaaaca tcaaccagaa aaattaagga ctctgctagc tatttggttt
 961 gtttgtttgt ttgtttgttt gtttgttttt gtaataatgg ggtctgcaca caggaccaat
1021 gctgctccat gctaggcaag tttgatcact gaactctatt tctagcactc ttctcgcttt
1081 ttatgttgag ccacaatctt accaacttgc tccggctggc cttgaactca ctttgtaatc
1141 cctacaagcc ctgaacttaa aattctcctg tcttggtctc cggaataggt ctgcctcacc
1201 atgccagttt gtattattac tgataacagt aaaatctgta aatgctgcat atactaaaca
1261 cttcccaaac atccctcatt tagcctctgt ggcagatttt ctactaaccc cggtttacct
1321 aagaatcaag gaaggctggg ggaagttaag acattcctcc actggcctgg agagatgact
1381 cagaggttaa gagcatttgc tgtcctttca gaggacccag attcaagtcc cagttcccac
1441 gtggcagctt agaatcatct gtaactccag ttccaagagc tctggcaccc tcttctgacc
1501 tcagcaggca caaagcatgc gggtacagca catacacaat gcaggcaaga cattcattca
1561 caataaatta gttttgtttt gatttttttag gaactacttt tctccaaagt aaattgctgg
1621 agtccattgc caggctatcc taaacaccag tggcagaaga cattttcata agcccccaa
1681 tgatttcctc aactgccttt ctaatcagct aaacaactaa gtctgacttc gcctcaagta
1741 tattttacta ctctttgttt tagggtaagt tggtggtctt agtagagcac tttgagtttg
1801 gttaaaaatt aacagttgca aatttagaaa cactgttacc ttaggcactg ccatcttaga
1861 agcctaggag tcagggggat cctggacacc acaagaaaac aacccacagc atcaactaag
1921 cagggctcat aggcgctcac agaaactgaa gcggctagca cagggcctac gtgtgtctgt
1981 gctaggttct ctgtgtatgt gttatggttg tgtagcttgg tggtcttgta gaagttgttt
2041 tcttaggtaa atgttatttg tttaatattg gaataaaact aagaaacctt tctggcctgg
2101 gaagccatgt ttctgcccag gaacacagag cacctccagc agctgtctgc tttgaagctg
2161 ctaagagctc gctcaggaag aagtgaagtc atccgcttct atctatcttc tatctataac
2221 gatggcacaa cggttcagta attttgccac aggacagcag aaatgaaggg cgaagaaaaa
2281 ggcgagctgg caatcacttt atttcagttc acttcagtca aacccttgct cccatttttt
2341 ttttttctag tgtgatttca cacaaagtga ctcatgaaaa ttgcacgcat atgtggggag
```

Figure 15B

```
2401 attagcaata ccggacttca gtgacactga ggccggcttc cattccattc cacttatatt
2461 gacagctgaa cagctgcttt tttttttttt tttttttttt tttttttttt tttttctcc
2521 cttcagggca aagaacacac acaagcgatg tgtttaaaaa gagatggttt gtatttaaac
2581 tgccagagag aactgacacc acctttagtt taggtagggg atttccgcta gttactttt
2641 gtcctaacat tggataaagc ccactgctct gagtcactaa ccacttccag ccaatcacag
2701 acagaccaac acacccgccc gcagccaatt ttctgagccc tgccgtgctt taaccgcaga
2761 accaatccga aggacccgct gtcatctttc atccagctgg ttgtcgctgc cgccgcctcc
2821 agattccgaa ggcgaagctc gcgaagcag
```

STXBP1 OVEREXPRESSING MOUSE AND ITS USES IN SCREENING OF TREATMENTS FOR NEUROPSYCHIATRIC ILLNESS

CROSS REFERENCE TO RELATED APPLICATIONS

This is the U.S. National Stage of International Application No. PCT/EP2009/060674, filed Aug. 18, 2009, which was published in English under PCT Article 21(2), which in turn claims the benefit of U.S. Provisional Application No. 61/090,607, filed Aug. 20, 2008, which is incorporated herein in its entirety.

FIELD OF THE INVENTION

The present invention relates to a marker for psychiatric illness, particularly schizophrenia and bipolar disorder, to animal models utilising the marker and to methods of screening for agents that affect the marker and which may have therapeutic potential.

BACKGROUND TO THE INVENTION

Psychiatric disorders such as schizophrenia are becoming one of the major public-health problems on a global scale. The causes of these disorders are as yet poorly understood, although genetic factors undoubtedly play an important role in their aetiology. Furthermore, this illness does not develop because of the alteration of one single gene but more likely due to changes in a group of genes, which makes this a multi-factor illness.

According to the WHO, around 24 million people are currently suffering from schizophrenia, which is approaching 1% of the world's population, and its prevalence is similar in both men and women. Schizophrenia generally appears at the end of adolescence or early in adult life, and it produces profound changes in thought processes, perception and emotions. Its progress varies, and it can range from a single episode with complete recovery to a serious deterioration and suicide. Although patients with schizophrenia represent less than 40% of those that require psychiatric hospitalisation, the morbidity and chronicity experienced by patients with schizophrenia mean that it has become the most serious and incapacitating mental illness of early and middle adult life. Indeed, the direct cost of schizophrenia in industrialised countries has been estimated to be between 1.6 and 2.6% of total health expenditure [Rössler, 2005].

The classical neurobiological hypothesis to explain schizophrenia invokes hyperactivity of the brain's dopaminergic system. Antipsychotic drugs would therefore produce their therapeutic effect by antagonising these dopamine receptors. This hypothesis was subsequently refined by suggesting that hypoactivity of the cortical glutamatergic system could be responsible for the dopaminergic hyperactivity observed in schizophrenia. Indeed, control of the sub-cortical dopaminergic system by the cortical glutamatergic system might be consistent with the classical postulates. Recent studies have demonstrated important neuronal and/or glial deficiencies in the cortex, possibly linked to changes in the early development of the nervous system associated with schizophrenia. It is therefore more likely that schizophrenia is caused by abnormal neuronal connections rather than by neuronal loss [Horner, 2002].

Genetic studies have identified a number of susceptibility genes linked to schizophrenia [Weinberger, 2005]. Despite this, reliable biomarkers for schizophrenia are currently lacking. One of the candidate molecular substrates for a type of abnormal neuronal connectivity is a group of neuronal proteins known as SNARE (soluble N-ethylmaleimide-sensitive factors attachment protein receptors), which serve as a fundamental elements in the molecular control of neurotransmission [Sollner, 1993a; Sollner, 1993b]. This neurotransmission process is activated in response to an influx of $Ca^{2+}$ activated by an action potential provoking the fusion of the synaptic vesicles containing the neurotransmitters with the pre-synaptic membranes and the release of their content into the synaptic cleft, where these molecules diffuse towards the post-synaptic terminal. Two types of SNARE proteins have been identified depending on their sub-cellular location: a) v-SNARE proteins, which were first described in the neurotransmitter vesicles and which include the VAMP/synaptobrevin protein; and b) t-SNARE proteins, which were first described in the pre-synaptic region of the target plasma membrane and that include syntaxin and the synaptosomal-associated protein of 25 kDa, or SNAP25. This group of proteins is characterised by having a conserved region of about 60 amino acids, known as the SNARE motif, and they generally possess a region involved in membrane anchoring. It is currently thought that SNARE proteins are intimately involved in membrane fusion, although they require other accessory proteins for their activity. These accessory proteins include N-ethylmaleimide-sensitive factor or NSF (an ATPase associated with a variety of cell activities) and the family of SM proteins, which contains the Sec1p protein and Munc-18 protein (also known as syntaxin binding protein 1 (STXBP1)). These proteins are essential for membrane fusion as this event is much slower in vitro in their absence. The role of STXBP1 in neurotransmitter release has been clearly demonstrated by a series of experiments showing that there is no vesicular synaptic transmission during the development of animals that do not express the gene encoding this protein [Verhage, 2000]. The most widely accepted model to explain the molecular mechanism of vesicular neurotransmitter release suggests that STXBP1 binds to syntaxin, thereby inhibiting the binding of this protein to the rest of the SNARE complex. When STXBP1 is freed from its association with syntaxin, the latter can interact with SNAP25 and VAMP to form the SNARE complex. When coupled with an increase in intracellular calcium, this complex is responsible for promoting the docking of the vesicles to the plasmatic membrane, thereby inducing the release of neurotransmitters from the synaptic vesicles [Voets, 2001].

Several recent studies have demonstrated that some psychiatric and neurodegenerative illnesses show changes in the expression (both of messenger RNA and the protein) of certain components of the SNARE complex. For example, changes in the levels of VAMP and SNAP-25 proteins have been found post-mortem in the prefrontal cerebral cortex of human schizophrenic patients [Honer, 2002; Halim, 2003]. Similarly, abnormal levels of SNAP-25 have been found post-mortem in the hippocampus and cerebellum of schizophrenic brains [Young, 1998; Fatemi, 2001; Mukaetova-Landiska, 2002], and other groups have found abnormal SNAP-25 levels in the cerebrospinal fluid of patients diagnosed with schizophrenia [Thompson, 2003]. Significant schizophrenia-associated changes were, however, not found in NSF proteins, which are also associated with the SNARE complex [Imai, 2001; Gray, 2006]. Increased expression of STXBP1 has been reported in membrane microdomains of dorsolateral prefrontal cortex from schizophrenic patients [Behan, 2008]. However, down-regulation of STXBP1 has been reported in postpubertal neonatally ventral hippocampal (nVH) lesioned rats, an extensively used neurodevelopmental model of schizophrenia-like behaviours [Vercauteren, 2007].

Mouse models that mimic the full phenotypic spectrum of a psychiatric disorder, such as schizophrenia, are virtually impossible. However, a recreation of some phenotypic components is feasible and animal models of schizophrenia often try to mimic some of the positive and/or negative symptoms of the disorder. In this context, animal models have a central role in discovering the causes of psychiatric disorders and generating novel mechanism-based treatments [Arguello & Gogos, 2006]. Transgenic animals are desired as a method of studying functions of genes in a living body, or as a model animal for developing therapeutic agents. However, it is difficult to prepare a model reflecting a human disease having a mechanism of development which is unknown, such as schizophrenia. Furthermore, finding animal correlates of the positive symptoms of schizophrenia (such as paranoid delusions, hallucinations, and disordered speech and thinking) is challenging. Nevertheless, hyperactivity in response to stress or novelty have been suggested as useful correlates that can be modelled in rodents and have been extensively used in the validation and assessment of pharmacological models [Geyer and Moghaddam, 2002]. Less extensively modelled are the negative symptoms (such as blunted emotional expression, low motivation, and social withdrawal). These symptoms represent a significant portion of the psychopathology in major depression and, considering the substantial comorbidity between schizophrenia and depression, many of these deficits may be secondary symptoms in schizophrenia [Ellenbroek and Cools, 2000]. Impaired social interactions, anxiety and depression-like behaviour in animals are often used to model negative symptoms of schizophrenia. Moreover, schizophrenia patients display various forms of memory deficits including impaired working and episodic memory. To date, there are numerous working memory tasks employed in animals, such as novel object recognition task. Almost all behavioural animal models include a locomotor component. For this reason, it is important to assess the locomotor activity of the animals to be tested before applying the test to discard the possible limitations in the movement ability of the transgenic mice.

There is at present an unmet need for animal models of schizophrenia. A significant difficulty remains the translation of genetic association studies into models that are effective for evaluating the efficacy of candidate therapeutic compounds. In particular, the complexity of the disorder means that it is not normally possible to predict whether a genetic alteration associated with the disorder has a causal role and will produce behavioural changes of relevance to schizophrenia.

DISCLOSURE OF THE INVENTION

The present inventors have now found that STXBP1 is expressed much more strongly in the prefrontal cortex of schizophrenics who died by suicide and who were not undergoing drug treatment when compared with samples taken from the same brain region of control individuals with no history of mental illness and who died accidentally. Interestingly, the STXBP1 levels in schizophrenic patients undergoing treatment with antipsychotic drugs who died by suicide were found to be lower than those of untreated schizophrenics, and they were similar to those of the control subjects. Furthermore, the findings disclosed herein indicate that enhanced expression of STXBP1 is not merely a consequential change associated with schizophrenia, but appears to have a causal role, as shown by schizophrenia-related behavioural changes in transgenic mice that overexpress STXBP1 in the frontal cortex. The difference observed in STXBP1 levels in drug-treated and drug-free schizophrenics makes STXBP1 an attractive drug target and screening tool for candidate therapeutics for psychiatric conditions, including schizophrenia.

Accordingly, in a first aspect the present invention provides a non-human transgenic animal having a polynucleotide encoding an STXBP1 polypeptide, which polynucleotide is operably linked to a promoter, wherein said transgenic animal has greater than wild-type expression of the STXBP1 polypeptide in at least one brain region. Preferably, the transgenic animal exhibits one or more schizophrenia-related behaviours, for example: reduced motor activity in an open-field test; reduced time spent in open arms of an elevated plus maze; reduced social interaction; and increased recognition index in a novel object recognition task.

The transgenic animal of the invention may contain a foreign gene or promoter (i.e. genetic material from another species) or it may not contain any foreign gene or promoter. The latter case is considered transgenic herein by virtue of an alteration in the location, copy number or sequence of an STXBP1-encoding polynucleotide and/or an alternation in the promoter controlling expression of the STXBP1-encoding polynucleotide. In certain cases, the transgenic animal of the invention may have said polynucleotide encoding an STXBP1 polypeptide present in a higher than wild-type copy number. For example, the transgenic animal may carry a native or non-native stxbp1 gene in higher than diploid copy number. The transgenic animal of the invention may have the polynucleotide encoding an STXBP1 polypeptide operably linked to a promoter which is other than an stxbp1 gene promoter. Thus, for example, the promoter may be an endogenous or exogenous promoter from another gene, preferably a promoter from a gene which exhibits brain-specific or largely brain-specific expression.

In certain cases of the transgenic animal according to the invention said polynucleotide encodes an STXBP1 polypeptide which is a mouse, rat or human STXBP1 polypeptide, a variant (such as a splice variant), derivative (such as a post-translationally processed polypeptide), homologue or orthologue from another species (preferably a mammalian homologue or orthologue) or fragment. The STXBP1 polypeptide or fragment thereof preferably exhibits biological activity, particularly the ability to bind to a syntaxin polypeptide. In preferred cases of the transgenic animal according to the invention said polynucleotide encodes:
  (i) an STXBP1 polypeptide having an amino acid sequence having at least 80%, 90%, 95% or 99% amino acid sequence identity to the sequence of SEQ ID NO: 2;
  (ii) an STXBP1 polypeptide having the amino acid sequence of SEQ ID NO: 2
  (iii) an STXBP1 polypeptide having an amino acid sequence having at least 80%, 90%, 95% or 99% amino acid sequence identity to the sequence of SEQ ID NO: 4;
  (iv) an STXBP1 polypeptide having the amino acid sequence of SEQ ID NO: 4; or
  (v) an active fragment of any one of (i)-(iv) having at least 200, 250, 300, 350, 400, 450, 500 or 550 amino acids, wherein said STXBP1 polypeptide of any one of (i)-(iv) or said active fragment of (v) is capable of binding to a syntaxin polypeptide.

In certain cases of the transgenic animal according to the invention said promoter is a brain-specific promoter. Preferably, the promoter is specific for glutamatergic neurons. A particularly preferred promoter is the promoter of the EAAT3 gene, especially an EAAT3 promoter of the same species as the transgenic animal. The EAAT3 promoter may comprise or consist of a polynucleotide having at least 80%, 90%, 95% or 99% nucleotide sequence identity to the sequence of SEQ ID NO: 6 or may comprise or consist of a polynucleotide having the sequence of SEQ ID NO: 6. The present inventors have found that the EAAT3 promoter permits elevated expression of STXBP1 in a targeted manner; expression is largely confined to glutamatergic neurons. Thus, use of the EAAT3 promoter to drive expression of STXBP1 provides an advantageous way to induce the desired schizophrenia-like phenotype of certain embodiments of the transgenic animal of the invention.

Preferably, the transgenic animal of the invention has greater than wild-type expression of the STXBP1 polypeptide, as defined herein, in at least one brain region selected from: cortex, striatum, hippocampus and cerebellum. Results disclosed herein indicate that elevated expression of STXBP1 in one or more of these brain regions contributes to or underlies the schizophrenia-like phenotype observed. The elevated expression may in some cases be a relatively modest increase in expression compared with wild-type (e.g. compared with the expression in the same brain region of a species-, gender- and age-matched wild-type animal which does not carry any genetic alteration relating to STXBP1 or its promoter). In some cases elevated expression may be at least 10%, 20%, 30%, 50% or greater expression of the STXBP1 polypeptide in said at least one brain region. A variety of techniques are available for measuring expression of STXBP1, including techniques for direct measurement of protein levels (e.g. Western blot, immunofluorescence) and techniques for indirect measurement based on measurement of mRNA encoding the STXBP1 polypeptide (e.g. qPCR).

As used herein in relation to this and other aspects of the present invention, greater or elevated expression of STXBP1 may include elevated expression in a cytosolic fraction, a non-cytosolic fraction or both cytosolic and non-cytosolic fractions of one or more brain regions. Without wishing to be bound by theory, it is presently believed that a redistribution of STXBP1 from a membrane fraction to a cytosolic fraction may contribute to or underlie schizophrenia.

The transgenic animal of the invention is preferably a rodent, such as a mouse or rat. In some cases the transgenic animal of the invention may be a non-human primate or other laboratory animal such as a dog or cat. Most preferably, the transgenic animal is a mouse (e.g. *Mus musculus*).

In a second aspect the present invention provides a vector comprising a polynucleotide encoding an STXBP1 polypeptide operably linked to a brain-specific promoter which is other than an stxbp1 gene promoter and, optionally, further regulatory sequences. Preferably, said polynucleotide encodes an STXBP1 polypeptide which is a mouse, rat or human STXBP1 polypeptide, a variant (such as a splice variant), derivative (such as a post-translationally processed polypeptide), homologue or orthologue from another species (preferably a mammalian homologue or orthologue) or fragment. The STXBP1 polypeptide or fragment thereof preferably exhibits biological activity, particularly the ability to bind to a syntaxin polypeptide. In preferred cases of the vector of this aspect of the invention said polynucleotide encodes:
  (i) an STXBP1 polypeptide having an amino acid sequence having at least 80%, 90%, 95% or 99% amino acid sequence identity to the sequence of SEQ ID NO: 2;
  (ii) an STXBP1 polypeptide having the amino acid sequence of SEQ ID NO: 2
  (iii) an STXBP1 polypeptide having an amino acid sequence having at least 80%, 90%, 95% or 99% amino acid sequence identity to the sequence of SEQ ID NO: 4;
  (iv) an STXBP1 polypeptide having the amino acid sequence of SEQ ID NO: 4; or
  (v) an active fragment of any one of (i)-(iv) having at least 200, 250, 300, 350, 400, 450, 500 or 550 amino acids, and wherein said STXBP1 polypeptide of any one of (i)-(iv) or said active fragment of (v) is capable of binding to a syntaxin polypeptide.

Said promoter of the vector of this aspect of the invention may be specific or largely specific for glutamatergic neurons. A preferred promoter of the vector of this aspect of the invention is an EAAT3 promoter. The EAAT3 promoter may comprise or consist of a polynucleotide having at least 80%, 90%, 95% or 99% nucleotide sequence identity to the sequence of SEQ ID NO: 6 or may comprise or consist of a polynucleotide having the sequence of SEQ ID NO: 6.

In a third aspect the present invention provides a method for producing a transgenic animal of the invention, comprising:
  introducing a vector of the second aspect of the invention into one or more cells of the animal at an embryonic stage; and
  optionally, subsequently extracting DNA from the animal to confirm the incorporation of the polynucleotide into the genome of the animal. The method of this aspect of the invention may further comprise breeding heterozygous transgenic animals produced by the method of this aspect of the invention in order to produce offspring, in particular offspring homozygous or heterozygous for the incorporated polynucleotide.

In a fourth aspect the present invention provides an in vitro method for identifying an agent (e.g. a small molecule, a nucleic acid or a protein) for use in the treatment of neuropsychiatric illness, particularly schizophrenia and/or bipolar disorder, comprising:
  (i) contacting a cell that expresses an STXBP1 polypeptide with a test agent and measuring, directly or indirectly, expression of the STXBP1 polypeptide relative to expression of the STXBP1 polypeptide in a control cell which has not been exposed to the test agent; and/or
  (ii) contacting an STXBP1 polypeptide with a test agent and measuring, directly or indirectly, binding of the STXBP1 polypeptide to a syntaxin polypeptide relative to the binding of a control STXBP1 polypeptide which has not been exposed to the test agent to a syntaxin polypeptide,
  wherein a reduction in said expression in (i) and/or a reduction in said binding in (ii) due to the test agent indicates that the test agent is potentially useful in the treatment of neuropsychiatric illness, particularly schizophrenia and/or bipolar disorder. Preferably, said cell that expresses an STXBP1 polypeptide is a neuronal cell or non-neuronal cell obtained from:
  a patient having a neuropsychiatric illness, particularly schizophrenia or bipolar disorder; or
  a transgenic animal of the invention; or
  a cell that has been transfected or transformed with a polynucleotide encoding an STXBP1 polypeptide or with a vector in accordance with the second aspect of the invention.

Expression of STXBP1 polypeptide may be measured at any stage of expression of the STXBP1-encoding gene (e.g. measuring mRNA level or protein level). In preferred cases of the method of this aspect of the invention the test agent is found to reduce said expression in (i) and/or said binding in (ii). Such test agents may be regarded as functional antagonists of the STXBP1 polypeptide (whether they act pre- or post-translationally). Test agents that are found to reduce said expression in (i) and/or said binding in (ii) may be subjected to further screening (including in vivo screening as described further herein). In some cases the method of this aspect of the invention which further comprises isolating the test agent and, optionally, formulating the test agent into a pharmaceutical composition with at least one pharmaceutically acceptable salt, carrier or excipient.

In a further aspect the present invention provides an in vitro screening method comprising:
- contacting at least one cell that expresses an STXBP1 polypeptide with a test agent; and
- detecting whether said test agent alters an STXBP1-related activity as compared with said activity in the absence of the test agent.

The method may comprise detecting a change in STXBP1-related activity in the presence of the test agent as compared with said STXBP1-related activity in the absence of the test agent. The method may comprise comparing the STXBP1-related activity of a cell exposed to the test agent with said STXBP1-related activity of a (second) "control cell" which has not been exposed to the test agent. Additionally or alternatively, the method may comprise comparing the STXBP1-related activity of a cell exposed to the test agent with said STXBP1-related activity of the same cell in the absence of the test agent. For example a "baseline" of said STXBP1-related activity may be established prior to addition of the test agent and the STXBP1-related activity assessed (e.g. relative to said baseline) after exposing the cell to the test agent. Preferably, the cell is a cell that has been transfected or transformed with a vector comprising a polynucleotide that encodes said STXBP1 polypeptide, e.g. a vector in accordance with the second aspect of the invention. In particular, the cell may be a neuronal cell line (e.g. a human or animal, such as rodent, derived cell line) or a stem cell-derived neuronal cell. The altered STXBP1-related activity may be selected from: altered binding of STXBP1 to syntaxin; altered syntaxin binding to a SNARE complex; altered synaptic vesicle-plasma membrane fusion; altered synaptic vesicle exocytosis; and altered neuronal signalling. For example, the method may comprise detecting a change in the synaptic vesicle release process (e.g. increased or decreased synaptic vesicle release) in the presence of the test agent as compared with the synaptic vesicle release in the absence of the test agent. Preferably, the test agent is found to inhibit at least one STXBP1-related activity. The cell used in the method according to this aspect of the invention may comprise a vector comprising a polynucleotide that encodes an STXBP1 polypeptide operably linked to a promoter, such as a promoter that permits variable expression of the STXBP1. The promoter may be an EAAT3 promoter as defined in accordance with the tenth aspect of the invention. Alternatively or additionally, a plurality of cells each comprising a vector comprising a polynucleotide that encodes an STXBP1 polypeptide operably linked to a promoter may be used in accordance with the method of this aspect of the invention. In some cases, the plurality of cells may comprise sub-sets of cells, wherein the cell of each sub-set has a vector having a promoter that differs from the promoter of the vectors of cells of other of said sub-sets, such that the expression level of STXBP1 differs between said sub-sets of cells. Preferably, a first sub-set of cells is characterised by relatively low expression of STXBP1 and a second sub-set of cells is characterised by higher expression of STXBP1 relative to said first sub-set of cells.

In a fifth aspect the present invention provides an in vivo method for identifying an agent for use in the treatment of neuropsychiatric illness, particularly schizophrenia and/or bipolar disorder, comprising:
(i) administering a test agent to a transgenic animal of the invention and subsequently measuring, directly or indirectly, the expression of an STXBP1 polypeptide in at least one brain region relative to the expression of the STXBP1 polypeptide in at least one brain region of a control transgenic animal of the invention, which has not been exposed to the test compound; and/or
(ii) administering a test agent to a transgenic animal of the invention and subsequently assessing the presence and/or severity of one or more schizophrenia-related behaviours in the transgenic animal relative to the one or more schizophrenia-related behaviours in a control transgenic animal of the invention, which has not been exposed to the test agent, wherein a reduction in said expression in (i) and/or said one or more schizophrenia-related behaviours in (ii) due to the test agent indicates that the test agent is potentially useful in the treatment of neuropsychiatric illness, particularly schizophrenia and/or bipolar disorder. Said one or more schizophrenia-related behaviours may be selected from: reduced motor activity in an open-field test; reduced time spent in open arms of an elevated plus maze; reduced social interaction; increased recognition index in a novel object recognition task; and decreased prepulse inhibition of startle response. Preferably, in the method of this aspect of the invention the test agent is found to reduce said expression in (i) and/or said one or more schizophrenia-related behaviours in (ii). Such test agents may be regarded as in vivo functional antagonists of STXBP1 and/or STXBP1-associated schizophrenia-like behaviour. In some cases the test agent is an agent which has previously been tested in a method of the fourth aspect of the invention. In this way an initial in vitro screen may be used to target subsequent in vivo screening on more promising candidate agents.

The method of this aspect of the invention may further comprise isolating the test agent and, optionally, formulating the test agent into a pharmaceutical composition with at least one pharmaceutically acceptable salt, carrier or excipient.

In a sixth aspect the present invention provides an agent identified or identifiable by a method of the fourth or fifth aspect of the invention. The agent may be for use in medicine. Preferably, the agent is for use in a method of treating a neuropsychiatric illness, particularly schizophrenia and/or bipolar disorder. Preferably, the agent comprises:
- an antibody molecule or binding fragment thereof capable of binding to an STXBP1 polypeptide (e.g. an STXBP1 polypeptide as defined in relation to any aspect of the present invention); or
- an antisense nucleic acid, ribozyme, triple helix molecule, siRNA or other nucleic acid capable of inhibiting STXBP1 gene expression (e.g. which is capable of hybridising to at least a portion of a polynucleotide that encodes an STXBP1 polypeptide as defined in relation to any aspect of the present invention or which is capable of hybridising to at least a portion of a polynucleotide which is complementary to the polypeptide that encodes the STXBP1 polypeptide).

In a seventh aspect the present invention provides use of an agent identified or identifiable by a method of the fourth or fifth aspect of the invention in the preparation of a medicament for treatment of a neuropsychiatric illness, particularly schizophrenia and/or bipolar disorder. Said agent may be as defined in relation to the sixth aspect of the invention.

In an eighth aspect the present invention provides a method for treating a neuropsychiatric illness, particularly schizophrenia and/or bipolar disorder, in a subject (e.g. a human patient in need of said treatment), comprising administering a therapeutically effective amount of an agent identified or identifiable by a method of the fourth or fifth aspect of the invention. Said agent may be as defined in relation to the sixth aspect of the invention.

In a ninth aspect the present invention provides a method of assessing the presence of or susceptibility to a neuropsychiatric illness, particularly schizophrenia and/or bipolar disorder, in a test subject, comprising:

detecting and/or determining the amount of an STXBP1 polypeptide and/or the amount of an mRNA or cDNA encoding an STXBP1 polypeptide in a sample which has been obtained from said test subject; and comparing said amount of the STXBP1 polypeptide and/or said amount of the mRNA or cDNA encoding the STXBP1 polypeptide with one or more reference values corresponding to the amount of the STXBP1 polypeptide and/or the amount of the mRNA or cDNA encoding the STXBP1 polypeptide in a control sample obtained from a control subject not having a neuropsychiatric illness. The sample may comprise blood, plasma, serum or tissue. Preferably, the sample comprises central nervous system tissue (e.g. prefrontal cortex tissue).

In certain cases of the method of this aspect of the invention the test subject has not previously been diagnosed as having a neuropsychiatric illness. In certain other cases of the method of this aspect of the invention the test subject has previously been diagnosed as having a neuropsychiatric illness. The method of this aspect of the invention may be used to assess the stage and/or severity of the neuropsychiatric illness or to monitor the effect of a treatment administered to the test subject.

In a tenth aspect the present invention provides a vector comprising a polynucleotide encoding a neuropathology-associated polypeptide operably linked to an EAAT3 promoter and optionally further regulatory sequences. Preferably, the EAAT3 promoter comprises or consists of a polynucleotide having at least 80%, 90%, 95% or 99% nucleic acid sequence identity to the sequence of SEQ ID NO: 6 or the EAAT3 promoter comprises of consists of a polynucleotide having the sequence of SEQ ID NO: 6. The polynucleotide encoding a neuropathology-associated polypeptide is preferably a gene, the elevated expression of which has been found to be associated with a neuropsychiatric illness (e.g. schizophrenia or bipolar disorder).

In an eleventh aspect the present invention provides use of a vector of the tenth aspect of the invention in the production of a transgenic animal having greater than wild-type expression of said neuropathology-associated polypeptide in at least one brain region. The transgenic animal so produced and its offspring may be utilised in screening of test agents for potential treatments of the neuropathology.

The present invention includes the combination of the aspects and preferred features described except where such a combination is clearly impermissible or is stated to be expressly avoided. These and further aspects and embodiments of the invention are described in further detail below and with reference to the accompanying examples and figures.

DESCRIPTION OF THE FIGURES

FIG. 2A) The non-normalised spot intensity values, and FIG. 2B) the values normalised by applying a base 2 logarithm, which gives a more homogeneous distribution.

FIG. 4A) Immunoreactivity for the STXBP1 protein determined in the cytosolic fraction of the prefrontal cortex (Brodmann area 9) of schizophrenic subjects who died by suicide (n=14) and separated into untreated (drug-free; DF, n=8) and treated with antipsychotic drugs (treated; T, n=6). The data are expressed as a percentage of the mean value±SEM (standard error) relative to controls fixed at 100±1%. The total group (All) of schizophrenic subjects (135±10%, n=14, +*p<0.004, one-sample t-test) and the group of untreated schizophrenic subjects give higher values than the controls (162±7%, n=8, +*p<0.0001, one-sample t-test). However, the group of treated subjects does not change with respect to the control group (100±9%, n=6, not significant). There is a significant difference between the STXBP1 levels in untreated and treated subjects, as determined by analysing the unidimensional variance (one-way ANOVA) and then applying a Bonferroni multiple comparison test (*p<0.01). FIG. 4B) Representative autoradiograms ("immunoblots") of the protein STXBP1 in post-mortem human brain (prefrontal cortex, Brodmann area 9) of untreated schizophrenic subjects who died by suicide (drug-free; DF), those treated with antipsychotic drugs (treated; T) and their respective controls (C). Brain samples containing 2 μg of total protein each were loaded onto 10% polyacrylamide gels. [C1=♂, 27 years, 10 hours PMD; DF1=♀, 25 years, 19 hours PMD; T1=♂, 30 years, 19 hours PMD; C2=♂, 28 years, 15 hours PMD; DF2=♀, 30 years, 13 hours PMD; T2=♂, 32 years, 8 hours PMD, where PMD is the time between death and autopsy].

FIG. 5A) Immunoreactivity for the STXBP1 protein determined in the non-cytosolic fraction of the prefrontal cortex (Brodmann area 9) of schizophrenic subjects who died by suicide (n=14), and separated into untreated (drug-free; DF, n=8) and treated with antipsychotic drugs (treated; T, n=6). The data are expressed as a percentage of the mean value±SEM (standard error) relative to controls fixed at 100±1%. The total group (All) of schizophrenic subjects (92±9%, n=13, not significant) and the group of untreated schizophrenic subjects (86±8%, n=8, not significant) are significantly lower than the controls. However, the group of treated subjects does not change with respect to the control group (101±22%, n=5, not significant). FIG. 5B) Representative autoradiogram ("immunoblots") of the STXBP1 protein in human brain post mortem (prefrontal cortex, Brodmann area 9) of untreated schizophrenic subjects who died by suicide (drug-free; DF), those treated with antipsychotic drugs (treated; T) and their respective controls (C). Samples containing 2 µg of total protein each were loaded onto 10% polyacrylamide gels. [C1=♂, 48 years, 16 hours PMD; DF1=F, 46 years, 19 hours PMD; T1=♂, 43 years, 65 hours PMD, where PMD is the time between death and autopsy].

FIG. 9A) Assessment of spontaneous locomotor activity in controls and transgenic mice in the open field. Motor activity was measured in a 5-min session, (n=6-7). Columns represent the means and vertical lines±SEM of steps in mice; * means values from transgenic mice that are significantly different (p<0.05, One-way ANOVA) in each line from control mice. FIG. 9B) Assessment of motor coordination in controls and transgenic mice in the rotarod test (n=6-7). Columns represent the means and vertical lines±SEM of time spent (seconds) in the rotarod. Assessment of anxiety-like behaviours in transgenic and wild-type mice in the elevated plus maze: FIG. 9C) Percent of time that mice remain in the open arms; FIG. 9D) Number of entries in open arms. Behaviour was evaluated for a period of 5 min. Columns represent the means and vertical lines±SEM of percentage of time in open arms in 5-7 mice; Values from transgenic mice (black columns) that are significantly different (*p<0.05, **p<0.006 One Way ANOVA) from control mice (white columns). FIG. 9E) Assessment of social interaction in transgenic and wild-type mice. Behaviour in each test was evaluated for a period of 5 min. Columns represent the mean and vertical lines±SEM of time (seconds) in 6-7 mice; * values from transgenic mice (black columns) that are significantly different (p<0.05, One Way ANOVA) from wild-type mice (white columns). FIG. 9F) Assessment of working memory performance in transgenic and wild-type mice. Behaviour in each test was evaluated for a period of 5 min. Columns represent the mean and vertical lines±SEM of recognition index in 5-7 mice; * values from transgenic mice (black columns) that are significantly different (p<0.05, One Way ANOVA) from wild-type mice (white columns).

FIGS. 10A to 10B show the mouse (Mus musculus) STXBP1 cDNA sequence available under NCBI Accession No. BC031728 [gi: 21594763] (SEQ ID NO: 1).

FIG. 11 shows the mouse (Mus musculus) STXBP1 predicted translated protein sequence available under NCBI Accession No. BC031728 [gi: 21594763] (SEQ ID NO: 2).

FIGS. 12A to 12B show the human syntaxin binding protein 1 (STXBP1), transcript variant 1 cDNA sequence available under NCBI Accession No. NM_003165 [gi: 4507296] (SEQ ID NO: 3).

FIG. 13 shows the human STXBP1 amino acid sequence available under Uniprot Accession No. P61764 (SEQ ID NO: 4).

FIGS. 14A to 14B show the mouse (Mus musculus) solute carrier family 1 (neuronal/epithelial high affinity glutamate transporter, system Xag), member 1, ("EAAT3") cDNA sequence available under NCBI Accession No. BC031728 [gi: 21594763] (SEQ ID NO: 5).

FIGS. 15A to 15B show the mouse (Mus musculus) promoter sequence of solute carrier family 1 (neuronal/epithelial high affinity glutamate transporter, system Xag), member 1, ("EAAT3") from the nucleotide 94024 to 96872 of the sequence GeneBank NCBI AC155724.8 [gi: 66793527] (SEQ ID NO: 6).

Figure 1:
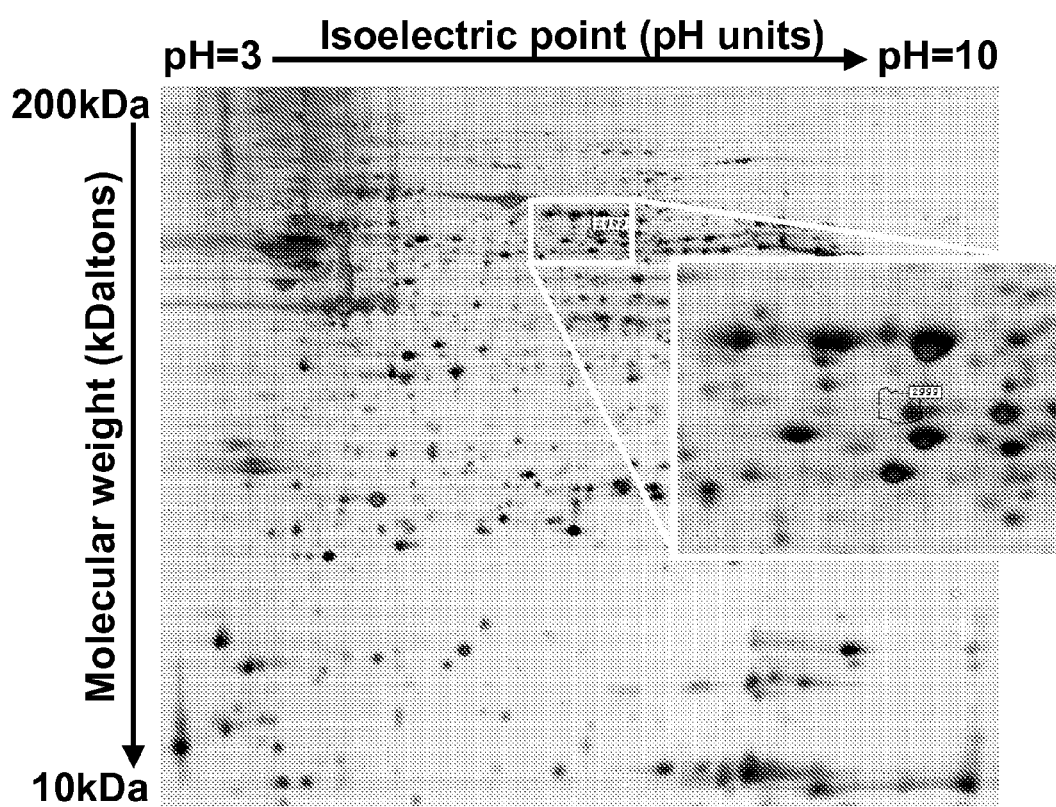
FIG. 1 shows a sample of human cerebral prefrontal cortex separated on a 2D polyacrylamide gel with a known pore size (12%) and stained with silver nitrate to visualise the proteins. The area containing the spots that correspond to the STXBP1 protein has been magnified.

The Sequence Listing is submitted as an ASCII text file in the form of the file named Sequence_Listing.txt, which was created on Feb. 16, 2011, and is 29,979 bytes, which is incorporated by reference herein.

DETAILED DESCRIPTION OF THE INVENTION

The terms "subject" or "individual" refer to members of mammalian animal species and include, but are not limited to, domestic animals, primates and humans; the subject is preferably a male or female human being of any age or race.

The term "neuropsychiatric illness" includes a wide range of undesirable psychiatric and neurological conditions, such as schizophrenia, bipolar disorder, major depression, schizoaffective disorder, psychiatric conditions (defined in the DMS IV manual) and neurological illnesses caused by alterations of the central nervous system.

The term "gene" refers to a region of a molecular chain of deoxyribonucleotides that encodes a protein and which could represent the complete coding sequence or a portion of it.

The term "DNA" refers to deoxyribonucleic acid. A DNA sequence is a sequence of deoxyribonucleotides.

The term "RNA" refers to ribonucleic acid. An RNA sequence is a sequence of ribonucleotides.

The term "mRNA" refers to messenger ribonucleic acid, which is the fraction of total RNA that is translated into proteins.

The term "cDNA" refers to a sequence of nucleotides that is complementary to an mRNA sequence.

The phrase "mRNA transcribed from" refers to the transcription of the gene (DNA) into mRNA, as the first step for the gene to be expressed and translated into protein.

The term "nucleotide sequence" refers equally to a sequence of ribonucleotides (RNA) or deoxyribonucleotides (DNA).

The term "protein" refers to a molecular chain of amino acids joined by covalent or non-covalent bonds. This term includes all types of post-translational modification, such as glycosylation, phosphorylation or acetylation.

The terms "peptide" and "polypeptide" refer to molecular chains of amino acids that represent a protein fragment. The terms "protein" and "peptide" are used indistinctly.

The term "antibody" refers to a glycoprotein that displays specific binding to a target molecule, which is termed the "antigen". The term "antibody" includes monoclonal antibodies or polyclonal antisera, either intact or fragments thereof; it includes human, humanised and non-human antibodies. "Monoclonal antibodies" are homogeneous populations of highly specific antibodies that target a unique antigenic site or "determinant". "Polyclonal antisera" include heterogeneous populations of antibodies that target different antigenic determinants.

The term "epitope", as used in the present invention, refers to an antigenic determinant of a protein, which is the amino acid sequence of the protein that a specific antibody recognises.

The term "solid phase", as used in the present invention, refers to a non-aqueous matrix to which an antibody can be bound. Examples of solid phase materials include glass, polysaccharides such as agarose, polyacrylamide, polystyrene, polyvinyl alcohol and silicones. Examples of solid phase forms are the well of a test plate or a purification column.

The terms "oligonucleotide" and "oligonucleotide primer" are used indistinctly and as used in the present invention, refer to nucleotide sequences that are complementary to a nucleotide sequence in the stxbp1 gene. Each primer hybridises with its target nucleotide sequence and acts as a starting point for nucleotide polymerisation catalysed by DNA polymerase, RNA polymerase or reverse transcriptase.

The term "probe", as used in the present invention, refers to a nucleotide sequence that is complementary to a nucleotide sequence derived from the stxbp1 gene and which can be used to detect this nucleotide sequence derived from the stxbp1 gene.

The term "therapeutic target" refers to nucleotide or peptide sequences against which a drug or therapeutic compound can be designed and applied clinically.

The term "antagonist" refers to any molecule that inhibits the biological activity of the antagonised molecule. Examples of antagonists include, amongst others, proteins, peptides, sequence variations of natural peptides and small organic molecules (molecular weights of less than 500 Daltons).

The term "exogenous promoter" as used herein means a promoter other than the STXBP1 gene promoter.

The term "to exhibit schizophrenic symptoms" means, but is no means limited to, particularly to show a reduction in the elevated plus maze as described below.

The term "model animal of schizophrenia" means an animal which may be used in detecting an effect of a test substance on the treatment for schizophrenia or screening for an agent for treating schizophrenia.

The term "negative symptoms" means, but is by no means limited to, particularly to exhibit disorder of social behaviour in the social behaviour test.

The term "cognitive impairment" means, but is by no means limited to, particularly to exhibit memory and learning disorders in the novel object recognition task as described below.

STXBP1

As used herein STXBP1 polypeptide may be a native STXBP1 polypeptide from a mammalian species, particularly a mouse, human or rat. STXBP1 is also known by the names: ANC18HA, Munc18-1, n-sec1, N-Sec1, NSEC1A, p67, rbSec1, rbSec1A, rbSec1B, Sect, Syntaxin-binding protein 1, Unc-18-1, Unc18a, Unc-18A and Unc-18 homolog. Also encompassed by the term STXBP1 polypeptide as used herein are variants (such as a splice variant), derivatives (such as a post-translationally processed polypeptide) and fragments thereof. The STXBP1 polypeptide or fragment thereof preferably exhibits biological activity, particularly the ability to bind to a syntaxin polypeptide such as syntaxin 1a (for example a syntaxin polypeptide of the same species). Preferably, the STXBP1 polypeptide has the ability to bind to a syntaxin polypeptide and to prevent or limit the ability of syntaxin to interact with component members of the SNARE complex. The STXBP1 polypeptide may comprise:
  (i) an STXBP1 polypeptide having an amino acid sequence having at least 80%, 90%, 95% or 99% amino acid sequence identity to the sequence of SEQ ID NO: 2;
  (ii) an STXBP1 polypeptide having the amino acid sequence of SEQ ID NO: 2;
  (iii) an STXBP1 polypeptide having an amino acid sequence having at least 80%, 90%, 95% or 99% amino acid sequence identity to the sequence of SEQ ID NO: 4;
  (iv) an STXBP1 polypeptide having the amino acid sequence of SEQ ID NO: 4; or
  (v) an active fragment of any one of (i)-(iv) having at least 200, 250, 300, 350, 400, 450, 500 or 550 amino acids, wherein said STXBP1 polypeptide of any one of (i)-(iv) or said active fragment of (v) is capable of binding to a syntaxin polypeptide.

As used herein an STXBP1-encoding polynucleotide or similar expression refers to any nucleic acid (DNA or RNA) that encodes an STXBP1 polypeptide as defined herein. Preferred STXBP1-encoding polynucleotides include those having at least 80%, 90%, 95% or 99% nucleotide sequence identity to the polynucleotide sequence of SEQ ID NO: 1 or 3. Particularly preferred STXBP1-encoding polynucleotides comprise or consist of a polynucleotide having the polynucleotide sequence of SEQ ID NO: 1 or 3.

EAAT3 Promoter

The nucleotide sequence of the mouse wild-type EAAT3 gene is shown in FIG. 14 (SEQ ID NO: 5). The nucleotide sequence of the wild-type promoter of the mouse EAAT3 gene is shown in FIG. 15 (SEQ ID NO: 6). The sequence spans nucleotides 94024 to 96872 inclusive, of the sequence of the GeneBank accession NCBI AC155724.8. This sequence covers the promoter and the 5"-untranslated region immediately upstream to the first initiating AUG codon of the EAAT3 gene.

As used herein the EAAT3 promoter may be a variant or homologue from a non-mouse species, wherein said variant or homologue comprises or consists of a polynucleotide sequence having at least 80%, 90%, 95% or 99% sequence identity to the polynucleotide sequence of SEQ ID NO: 6, or a fragment thereof having promoter activity. Preferably, the EAAT3 promoter comprises or consists of a polynucleotide sequence having the polynucleotide sequence of SEQ ID NO: 6.

Transgenic Animals

The non-human transgenic animal of the invention is preferably a rodent, most preferably a mouse. A variety of suitable techniques may be used to alter the mouse genome to enhance STXBP1 expression in at least one brain region. Preferably, a vector of the invention is introduced into a non-human embryo. The incorporated polynucleotide encoding an STXBP1 polypeptide and under control of a promoter is preferably transmissible between generations. This facilitates establishment of a colony of transgenic animals. Preferably, genomic incorporation of the polynucleotide is verified by extraction and characterisation of DNA from the transgenic animal and/or its offspring.

Screening Methods and Test Agents

When an agent reduces the expression levels of the stxbp1 gene or reverses the effects due to increased expression of said gene, this agent becomes a candidate for the treatment of neuropsychiatric disorders.

Thus, the invention relates to the use of nucleotide or peptide sequences from the stxbp1 gene in methods to search for, identify, develop and assess the efficacy of compounds to treat neuropsychiatric illnesses, especially schizophrenia. The importance of screening methods in the search for drugs based on the binding, competitive or otherwise, of a potential drug molecule to the therapeutic target should be stressed.

Another object of the invention consists of providing agents characterised by their inhibition of the expression and/or activity of the STXBP1 protein. Those agents which can be identified and assessed according to the present invention may be chosen from the group formed by:

a) a specific antibody, or combination of antibodies, against one or more epitopes present in the protein STXBP1, preferably a human or humanised monoclonal antibody, which can also include an antibody fragment, a simple chain antibody or an anti-idiotype antibody;

b) cytotoxic agents, such as toxins, molecules containing radioactive atoms, or chemotherapy agents, including but not limited to, small organic and inorganic molecules, peptides, phosphopeptides, antisense molecules, ribozymes, siRNAs, triple helix molecules, etc., which inhibit the expression and/or activity of the STXBP1 protein; and c) antagonists of the STXBP1 protein that inhibit one or more functions of said protein.

The crystal structure of squid neuronal Sec-1, a homologue of STXBP1 has been resolved [22; the contents of which are expressly incorporated herein by reference in their entirety]. Accordingly, a preferred test agent is a compound that binds to STXBP1 and prevents its interaction with one or more t-SNAREs from the syntaxin family. A test compound may be a compound which is predicted to bind to STXBP1 in the region of the effector-molecule binding-pocket formed by residues from domains 1 and 2 of STXBP1/Sec-1 [22]. Alternatively or additionally, a test compound may be a compound which is predicted to bind to STXBP1 in the syntaxin 1a interaction site which is involved in binding syntaxin 1a through contacts formed by residues from domains 1 and 3 of STXBP1/Sec-1 [22].

The present invention also provides a pharmaceutical composition that contains a therapeutically effective quantity of one or more agents identified in a screening method of the invention (in vitro or in vivo method) together with one or more excipients and/or transport substances. Furthermore, said composition may comprise a further active ingredient that inhibits the function of the STXBP1 protein.

The excipients, transport substances and auxiliary substances should be pharmaceutically and pharmacologically acceptable such that they can be combined with other components of the formulation or preparation and they do not cause adverse effects on the treated organism. The pharmaceutical compositions or formulations include those that are appropriate for oral or parenteral (including subcutaneous, intradermal, intramuscular and intravenous) administration, although the best administration route depends on the state of the patient. The formulations can be in the form of simple doses and the formulations are prepared according to known methods in the field of pharmacology. The amounts of active substances to be administered can vary depending on the therapeutic needs.

Diagnostic Methods

Methods of the present invention for assessing the presence of or susceptibility to a neuropsychiatric illness are based on the observation that subjects or individuals diagnosed with neuropsychiatric illnesses, especially schizophrenia, present much higher levels of the protein coded for in the stxbp1 gene (STXBP1 protein) than the corresponding levels in subjects with no clinical history of these illnesses.

The method presented involves a subject sampling step, and can work with different biological fluids such as, for example: blood, plasma, serum or cerebrospinal fluid. Preferably the sample comprises CNS tissue.

The samples can be taken from subjects previously diagnosed with a given neuropsychiatric illness or from undiagnosed individuals, as well as from a subject receiving treatment or who has been treated previously for a neuropsychiatric illness, particularly schizophrenia.

The present method may also involve an extraction step, either to obtain the protein extract from the sample or to obtain the total RNA extract.

Any conventional in vitro test can be used for measurement of levels of mRNA transcribed from the stxbp1 gene or its complementary cDNA, or the concentration of the STXBP1 protein, in samples collected from the individuals to be analysed and from control individuals.

Thus, in some cases the present invention provides an in vitro method for detecting the presence of neuropsychiatric illnesses in an individual, especially schizophrenia, to determine the state or severity of this illness in the individual, or to monitor the effect of a treatment administered to an individual who presents this illness, based either on measuring the concentration of the STXBP1 protein or the expression of the stxbp1 gene.

If the concentration of the STXBP1 protein is to be determined, the method may comprise an initial step where the protein extract from the sample is mixed with one or more specific antibodies against one or more epitopes of the STXBP1 protein, and a second step where the complexes formed between these antibodies and the protein STXBP1 are quantified.

A wide variety of immunological tests can be used to detect the formation of specific antigen-antibody complexes and several competitive and non-competitive protein binding assays have been described previously, a large number of which are available commercially.

Thus, the STXBP1 protein can be quantified with antibodies such as specific monoclonal and polyclonal antibodies, either intact or recombinant fragments thereof, combibodies, and Fab or scFv antibody fragments against the STXBP1 protein. These antibodies can be human, humanised or non-human in origin. The antibodies used in these tests can be labelled or not and the unlabelled antibodies can be used in clumping tests while the marked antibodies can be used in a wide range of tests. The labelling molecules that can be used to label the antibodies include radionuclides, enzymes, fluorophores, chemoluminescent reagents, enzymatic substrates or cofactors, enzyme inhibitors, particles, colorants and derivatives.

A wide range of well-known tests that use unlabelled (primary antibody) and labelled antibodies (secondary antibody) can be used with the invention dealt with hear. These techniques include the Western blot or Western transfer, ELISA (Enzyme-Linked immunosorbent assay), RIA (Radioimmunoassay), competitive EIA (competitive enzyme immunoassay), DAS-ELISA (double antibody sandwich-ELISA), immunocytochemical and immunohistochemical techniques, techniques based on the use of biochips or protein microarrays that include specific antibodies or tests based on colloidal precipitation in formats such as dipsticks. Other methods of detecting and quantifying the STXBP1 protein include affinity chromatography techniques, ligand binding tests or lectin binding tests.

If the mRNA or cDNA corresponding to the stxbp1 gene is to be detected in addition to or as an alternative to detecting the protein, the method of the invention may comprise extraction of RNA (such as total RNA). The mRNA or cDNA corresponding to the stxbp1 gene is detected by amplifying the total RNA extract or the corresponding cDNA synthesised by reverse transcription from the mRNA template in a first step, followed by a second step that involves quantification of the product amplified from the mRNA or cDNA from the stxbp1 gene. An example of mRNA amplification consists of reverse transcribing the mRNA into cDNA (RT), and then performing a polymerase chain reaction (PCR) with primer oligonucleotides. PCR is a technique that is used to amplify a certain nucleotide sequence (target) contained in a mixture of nucleotide sequences. PCR uses an excess of a pair of primer oligonucleotides that hybridise with the complementary strands of the target nucleotide sequence. Next, an enzyme with polymerase activity (Taq DNA polymerase) extends each primer by using the target nucleotide sequence as a template. The extension products are then converted into target sequences upon dissociation of the original target strand. New primer molecules then hybridise to them and the polymerase extends them. This cycle is repeated to increase the number of target sequences exponentially and it is a technique described in the U.S. Pat. No. 4,683,195 and U.S. Pat. No. 4,683,202. Many methods for detecting and quantifying the products of PCR amplification, any of which can be used in this invention, have been described previously. In a preferred method of the invention, the amplified product is detected by agarose gel electrophoresis as follows: five microliters of the amplification product is separated by electrophoresis on a 2% agarose gel in a TBE 0.5× buffer at 100 vdc for one hour. After electrophoresis, the gel is stained with ethidium bromide and the amplification product visualised by illuminating the gel with ultraviolet (uv) light. As an alternative to staining and also as a preferred technique, the amplification product can be transferred to a nylon membrane by the Southern blotting technique and detected with a specific, appropriately labelled probe for the cDNA of the stxbp1 gene.

In another example the mRNA is detected by transferring the mRNA to a nylon membrane by transfer techniques such as Northern blot and detection with specific probes for the mRNA or the corresponding cDNA for the stxbp1 gene. In another specific assay, the mRNA corresponding to the mucn18-1 gene may be amplified and quantified at the same time by real-time quantitative RT-PCR (Q-PCR).

The method may involve comparing the amount of the STXBP1 protein, the amount of mRNA from the stxbp1 gene or the amount of the corresponding cDNA detected in the sample taken from the subject with the amount of STXBP1 protein, the amount of mRNA from the stxbp1 gene or the amount of the corresponding cDNA detected in samples from one or more control subjects or with one or more pre-determined reference values. An increase of around 10%, preferably 20%, 30%, 50% or greater may indicate the presence of or susceptibility to a neuropsychiatric illness in the subject.

The following is presented by way of example and is not to be construed as a limitation to the scope of the claims.

EXAMPLES

Example 1

Analysis of Brain Tissue Using Bi-Dimensional Electrophoresis

Twenty four samples of human cerebral prefrontal cortex tissue (Brodmann area 9) from individuals diagnosed with schizophrenia who died by suicide or by natural or accidental causes (n=14) and from control subjects with no known psychiatric history who died of accidental or natural causes (n=10) were analysed. These samples were obtained from the Basque Institute of Legal Medicine (Instituto Vasco de Medicina Legal) under ethical and lawful conditions. The samples were processed and stored at −80° C. immediately after the autopsy (Table 1).

TABLE 1

Samples included in the study.

| Samples | Diagnosis | Cause of death | Sex (Male/Female) | Age (years) | Post-mortem Interval (hours) | Toxicology in plasma |
|---|---|---|---|---|---|---|
| PK 1 | Schizophrenia | Suicide | Male | 27 | 17 | Clozapine |
| PK 2 | Schizophrenia | Suicide | Male | 41 | 16 | (—) |
| PK 3 | Schizophrenia | Suicide | Female | 25 | 19 | (—) |
| PK 4 | Schizophrenia | Suicide | Male | 30 | 13 | (—) |
| PK 5 | Schizophrenia | Accidental | Female | 39 | 11 | (—) |
| PK 6 | Schizophrenia | Natural | Male | 43 | 65 | Clozapine |
| PK 7 | Schizophrenia | Natural | Male | 43 | 19 | (—) |
| PK 15 | Schizophrenia | Suicide | Male | 66 | 57 | Olanzapine |
| PK 18 | Schizophrenia | Suicide | Male | 57 | 19 | Quetiapine Phenobarbital |
| PK 19 | Schizophrenia | Suicide | Male | 48 | 19 | (—) |
| PK 21 | Schizophrenia | Suicide | Male | 30 | 19 | Olanzapine |
| PK 22 | Schizophrenia | Suicide | Male | 24 | 45 | (—) |
| PK 24 | Schizophrenia | Suicide | Male | 32 | 8 | Quetiapine, Lorazepan Paracetamol |
| PK 25 | Schizophrenia | Suicide | Male | 31 | 11 | (—) |
|  |  |  | 12 Males 2 Females | 38 ± 12 years | 24 ± 17 Hours |  |
|  | Control |  | Natural | Male | 30 |  |
| PK 8 |  |  |  |  | 10 | (—) |
| PK 9 | Control | Natural | Female | 30 | 15 | (—) |
| PK 11 | Control | Natural | Male | 27 | 10 | (—) |
| PK 12 | Control | Accidental | Female | 35 | 8 | (—) |
| PK 13 | Control | Accidental | Male | 38 | 59 | (—) |
| PK 14 | Control | Accidental | Male | 48 | 16 | (—) |
| PK 17 | Control | Accidental | Male | 70 | 41 | Alcohol |
| PK 20 | Control | Accidental | Male | 54 | 26 | (—) |

TABLE 1-continued

Samples included in the study.

| Samples | Diagnosis | Cause of death | Sex (Male/Female) | Age (years) | Post-mortem Interval (hours) | Toxicology in plasma |
|---|---|---|---|---|---|---|
| PK 23 | Control | Accidental | Male | 28 | 15 | Alcohol |
| PK 26 | Control | Accidental | Male | 32 | 28 | Alcohol, Amphetamine |
|  |  |  | 8 Males 2 Females | 39 ± 13 years | 23 ± 16 Hours |  |

In Table 1 the information associated with each sample is distributed in columns. The first of these corresponds to the diagnosis and is followed by the cause of death, sex, age, post mortem interval (PMI), and finally the toxicological data ((−) corresponds to negative toxicology).

The proteins were extracted from human cerebral prefrontal cortex tissue post mortem, and a volume of 1 ml of lysis buffer (urea 7M; thiourea 2M; CHAPS 2%, D-Streak 0.2%, 20 µl protease inhibitors) was added to 0.1 g of tissue. The mixture was sonicated in 20 second cycles for two minutes and then centrifuged at a speed of 75000 rpm for one hour at a temperature of 4° C. The supernatant was collected and the protein concentration determined using the Bradford test. The concentration range of the samples was between 2 and 12 µg/µl in an approximate volume of 1 ml.

Next, 250 µg of protein from each sample was resuspended in 450 µl of hydration buffer (urea 7M; thiourea 2M; CHAPS 2%, IPG buffer pH 3-10 2%, D-streak 2% and bromophenol blue 0.002%) and it was solubilised at room temperature for at least one hour.

Once all the samples had been solubilised, the proteins were separated in two dimensions by bi-dimensional electrophoresis. This technique involves two phases, a first phase in which the proteins and separated according to their charge (IEF, or isoelectric focusing) and a second phase in which they are separated according to their molecular weight (SDS-PAGE).

The IEF was performed on mini-gels that support an immobilised pH gradient (3-10). The first step consisted in introducing the previously solubilised proteins into the gel by applying a voltage of 30 V for 15 hours (active rehydration) and then gradually increasing the voltage to 8000 V. The IEF finished when the total volts reached 120,000. Under no circumstances can the resistance of each gel exceed 50 µA (microamps).

Separation of the proteins in the second dimension according to their molecular weight was performed on previously polymerised 12.5% acrylamide gels with dimensions of 26×20 cm (Ettan DALT twelve Gel Caster Amersham). Once the proteins had been separated, they were visualised by silver staining (Amersham). The result is a spot map in which each spot represents a protein (FIG. 1). The gels were scanned and analysed with specialist software (Progenesis PG 220 ver. 2006 from Nonlinear Dynamics). For this analysis, the images must be in a format of 300 dpi (dots per inch) and 8 bits/channel. The software delimits the outline of each spot and calculates its intensity as a function of area and grey scale, transforming the flat image into a volume. The result is a table which contains the number of spots with their intensity as a "raw value" obtained from each gel.

Example 2

Determination of STXBP1 as a Biological Marker for Schizophrenia

Figure 2:
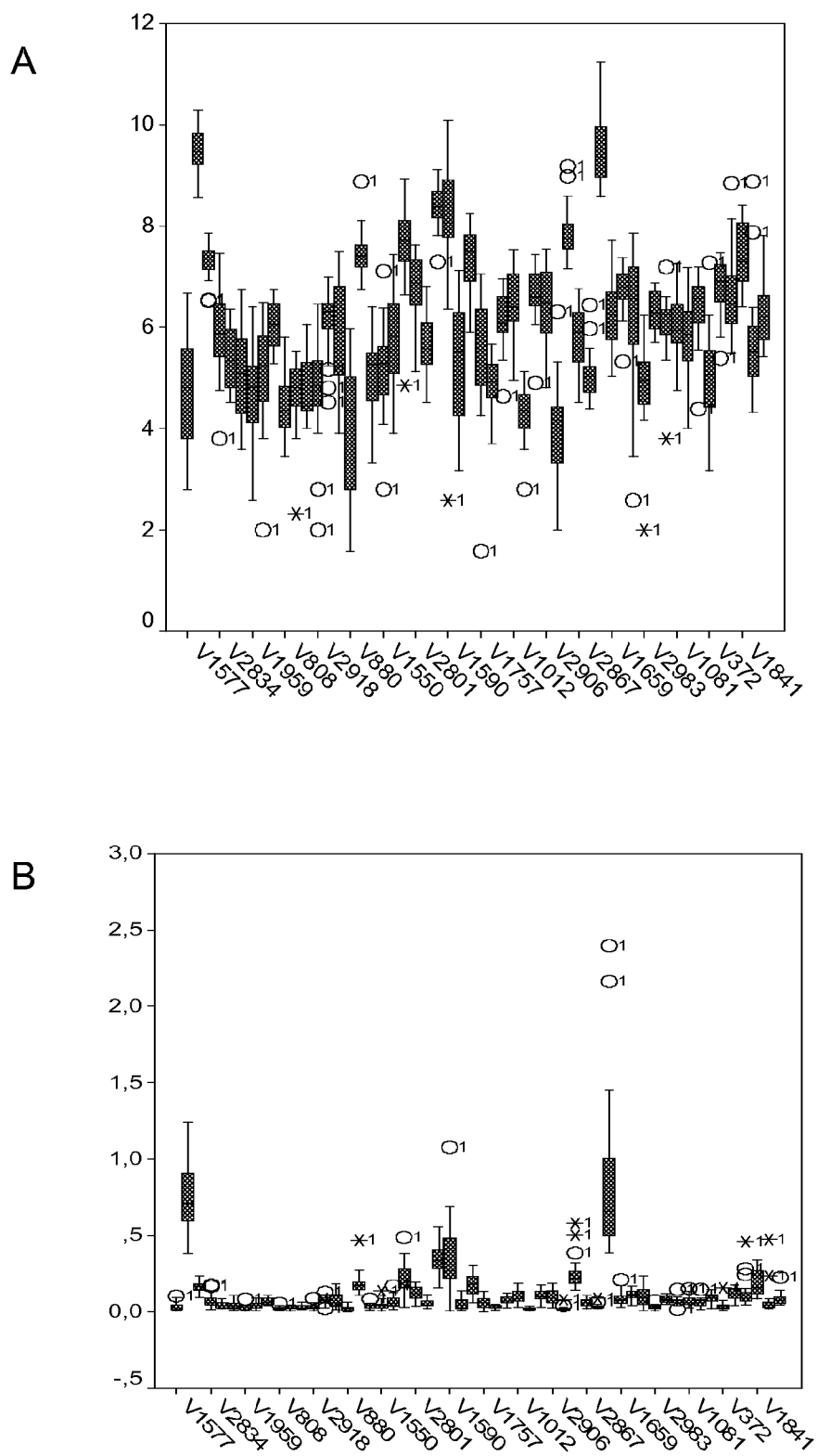
FIGS. 2A and 2B show box-and-whiskers plots of the spot intensities. The maximum and minimum values are given for each variable, along with the lower and upper quartiles (percentiles 75 and 25, respectively) and the median (percentile 50). The box is defined by the lower and upper quartiles and is crossed from one side to the other by the median. Lines extend from the box to the maximum and minimum values, and the values beyond the maxima and minima indicated by a circle are outliers.

A 2D map of the human prefrontal cortex was generated using the multiple 2D images that include both the common and additional spots found in all human brain samples. The data obtained were normalised experimentally by dividing the "raw" intensity of each spot by a certain value: the total spot volume and/or the spots that appeared in all samples. The object of this normalisation was to ensure that the differences observed are not due to different amounts of protein loaded onto the gels. The normalised data were exported to a MS Excel® sheet for statistical analysis. A large number of statistical tests require the data to follow a normal distribution. The spot/variable intensity distributions are clearly asymmetric and far from normal (FIG. 2, Graphic 1), although application of a logarithm homogenises and normalises these distributions (FIG. 2, Graphic 2).

The statistical analysis was undertaken by performing a parametric comparison test of the median values of the two groups established (total cases vs. controls or untreated cases vs. controls) and those spots with p≤0.05 were selected. The rate of change was calculated for the spots that were found to be significant by a quotient between the medians of the two established groups.

Those spots that were found to be significant were excised from the gels, digested in situ with trypsin and the peptides eluted and identified by MALDI-TOF (Matrix-Assisted Laser-Desorption/Ionization Time of Flight) mass spectrometry. The molecular mass fingerprint obtained for each spot was compared with an in silico database, which allowed the corresponding protein to be identified.

A total of 15 spots from the 24 gels (cases and controls) were matched and identified. The proteins were quantified as described previously and one spot (number 2999) was found to correspond to STXBP1 (FIG. 1).

Figure 3:
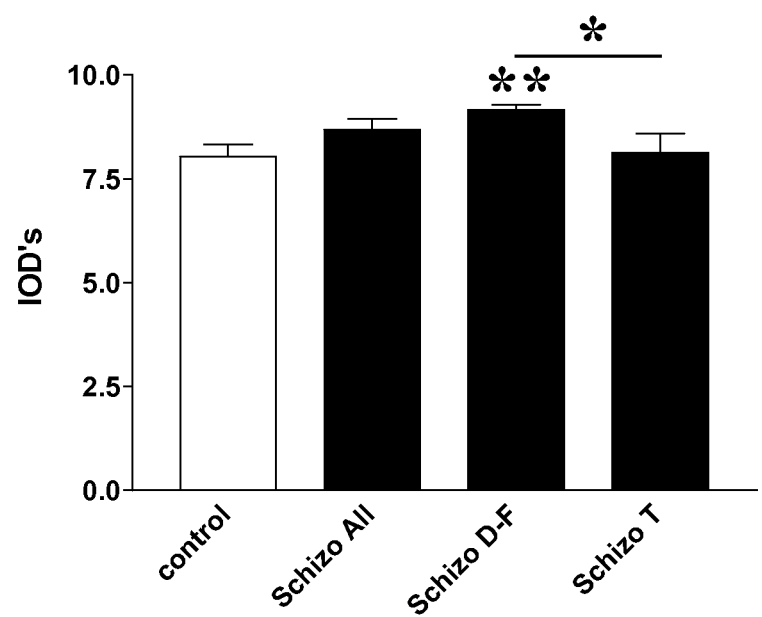
FIG. 3 shows a plot of the mean normalised optical intensity values obtained on bi-dimensional gels for the post mortem STXBP1 levels in the prefrontal cortex (Brodmann area 9) of human brain from control subjects (n=8), untreated subjects diagnosed with schizophrenia who died by suicide (n=7), or those treated with antipsychotic drugs (n=6). The data are given as a percentage of the mean value±SEM (standard error). It can be seen that the group of total schizophrenic subjects has a mean intensity higher than the controls (35%, n=14, p<0.004). When the group of total schizophrenic subjects is separated into untreated and treated a significant increase can be seen for the untreated subjects with respect to the controls (62%, n=8, p<0.0001), whilst the treated group remains at the same level as the controls.

The statistical analysis showed that only the comparisons between untreated or drug-free cases and controls, and untreated or drug-free cases and treated cases, produce a statistically significant difference (FIG. 3). The remaining comparisons, in other words total cases versus controls and treated cases versus controls, do not display significant changes (FIG. 3; only controls that were paired with either untreated or treated cases were used for the comparisons).

Example 3

Validation by Western Blotting of STXBP1 as a Biological Marker for Schizophrenia The levels of STXBP1 protein in 24 human cerebral prefrontal cortex samples (Brodmann area 9) from individuals diagnosed with schizophrenia who died by suicide and who had (n=6) or who had not (n=8) received antipsychotic treatment and control subjects with no history of psychiatric illness who died accidentally (n=10) were validated by Western blotting with an antibody that specifically recognises said protein. The samples from schizophrenics were paired with control samples on the basis of sex, age and time post mortem.

The proteins were then extracted using the same extraction procedure as that used to prepare the bi-dimensional gels. It was decided to measure the STXBP1 levels in both the cytosolic fraction and the membrane fraction for Western blot validation. Briefly, 1 ml of lysis buffer (urea 7M; thiourea 2M; CHAPS 2%, D-Streak 0.2%, 20 µl of protease inhibitors) was added to 0.1 g of tissue. The mixture was sonicated in 20 second cycles for two minutes and then centrifuged at a speed of 75000 rpm for one hour at a temperature of 4° C. The supernatant was collected and the protein concentration determined using the Bradford test. The pellet was resuspended in 100 µl of lysis buffer and the quantity of protein determined by the Bradford method. Laemmli 5× buffer (Tris 0.5M pH 6.8, SDS 20% and bromophenol blue 0.01%) was added just prior to loading the sample onto the gel. Once the sample had been prepared, β-mercaptoethanol was added at a ratio of 1/7. The total protein concentration was adjusted to 1.2 µg/µl for all the samples from the cytosolic fraction and to 0.5 µg/µl for those from the membrane fraction. Once prepared, the sample was heated to 100° C. for five minutes and then centrifuged for 15 seconds at 4° C. Two micrograms of total protein per sample was loaded onto a 10% acrylamide gel for both the cytosolic and the membrane fractions. A minimum of two experiments were performed for each sample and the arithmetic mean of all the individual values was calculated. A significant increase in the levels of STXBP1 protein was observed in the cytosolic fraction of prefrontal cortex samples from schizophrenic subjects when compared with the levels of the same protein in control subjects with no clinical history of psychiatric illness (135±10, n=14, $p<0.004$). Furthermore, it was found that the expression of STXBP1 protein was much higher in the prefrontal cortex of schizophrenics who had died by suicide and who had not received pharmacological treatment when compared with samples from the same brain region of control individuals with no history of psychiatric illness and who had died accidentally (162±7, n=8, $p<0.0001$).

Figure 4:
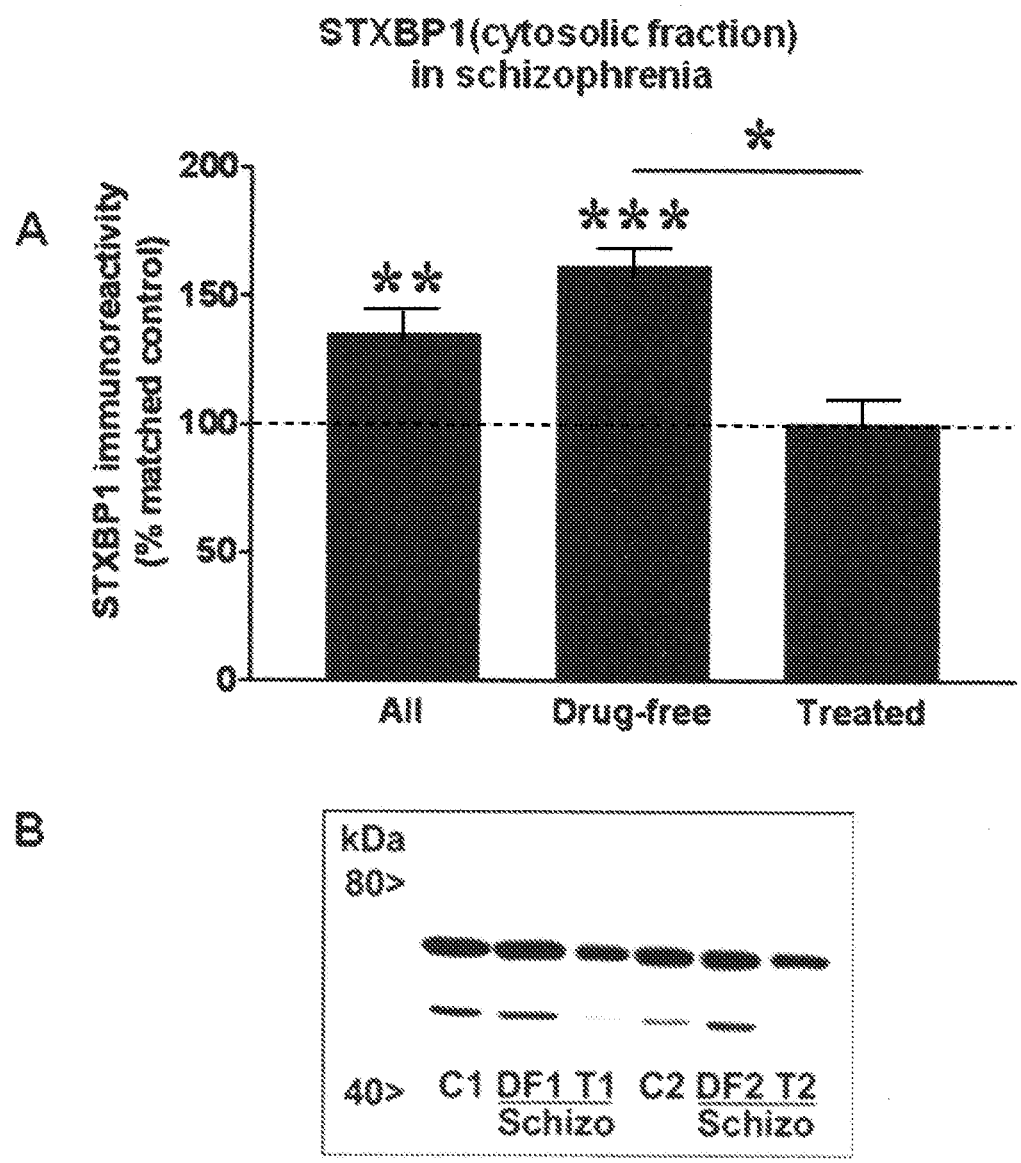
FIGS. 4A and 4B show quantification of STXBP1 in the cytosolic fraction.
Figure 5:
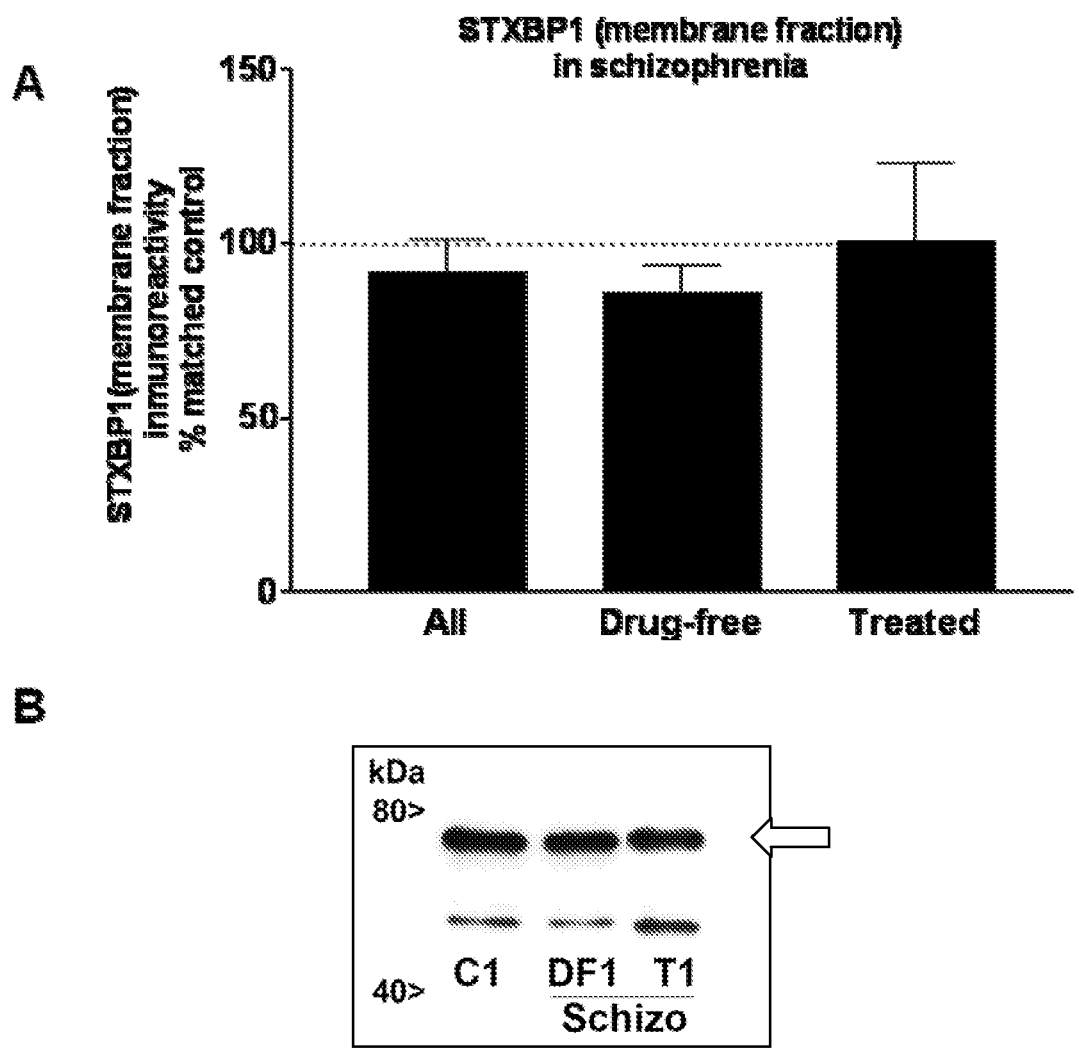
FIGS. 5A and 5B show quantification of STXBP1 in the membrane fraction.

Interestingly, it was found that the STXBP1 levels in schizophrenic subjects who had been treated with antipsychotic drugs but who had also died by suicide were lower than those in untreated individuals and were similar to the control levels (100±9, n=6, not significant; FIG. 4). On the other hand, it was found that there was a non-significant reduction in the density of the STXBP1 immunosignal in the non-cytosolic fraction of prefrontal cortex samples from schizophrenic individuals when compared with control subjects with no clinical history of psychiatric illness (92±9, n=13, not significant). Furthermore, STXBP1 expression was lower, although not significantly so, in the prefrontal cortex of schizophrenics who had not received pharmacological treatment when compared with samples from the same brain region of control individuals (86±8, n=8, not significant). Finally, there was no change in the STXBP1 levels in the group of subjects treated with antipsychotic drugs with respect to the control group (101±22, n=5, not significant; FIG. 5).

Example 4

Method of Preparing Transgenic Animal

The polynucleotide to be introduced contains a promoter sequence capable of controlling the expression of the schizophrenia-related protein and, if desired, may further contain an enhancer sequence. The schizophrenia-related protein may be expressed specifically in the brain. The promoter for preparing the model animal in the present example was specifically chosen. This promoter is the EAAT3 (Glutamate transporter type 3), also known which as solute carrier family 1 (neuronal/epithelial high affinity glutamate transporter, system Xag), member 1 (SLc1a1). The EAAT3 gene is a neuronal gene specifically expressed in glutamatergic neurons. Therefore, a desired gene (in this case STXBP1) can be selectively expressed in the brain, particularly in glutamatergic neurons, by using the promoter region of an EAAT3 gene. The transgenic mice were found to exhibit schizophrenic symptoms as a result of overexpression of STXBP1 in the brain.

To prepare the promoter region the primers used were: 5":ttgtcgacttcgcgagcttcgccttcggaatctggag (SEQ ID NO: 7); and 5":ttggtaccatagtccaaccagagacagagcacactc (SEQ ID NO: 8).

2848 nucleotides of the promoter of EAAT3 (SEQ ID NO: 6) (Glutamate transporter type 3), also known as solute carrier family 1 (neuronal/epithelial high affinity glutamate transporter, system Xag), member 1 (Slc1a1) (see FIG. 15) were amplified by a polymerase chain reaction (PCR). The neuronal expression promoter was cloned in Kpn I-Sal I in the right anterior position to the cDNA to be expressed (NIH_MGC_94) in the pCMV-Sport6 commercial vector. The construct was digested with Kpn I and Cla I to produce the transgene that was microinjected in mouse embryos. These transgene fragments, in addition to EAAT3 and cDNA contained a sv40 polyadenylated site for stabilizing the mRNA. Four transgenic founders were developed and three of them transmitted the transgene fragment: line 3 (L3), line 7 (L7) and line 8 (L8).

Figure 6:
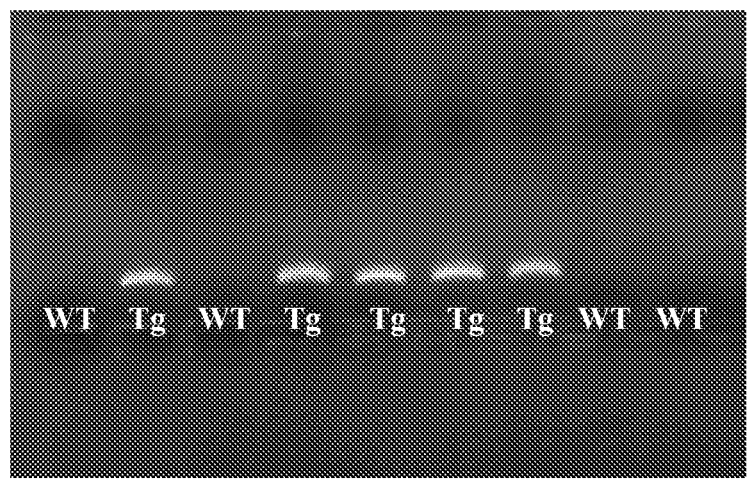
FIG. 6 shows agarose gel microphotography following PCR amplification (WT: wild type mouse; Tg: transgenic mouse).

Successful introduction of the gene may be determined by extracting DNA from a part of the body (for example the tail tip) and confirming the presence of the introducing polynucleotide. Animals testing positive for the introduced gene are regarded as founders. The introduced polynucleotide is transmitted to 50% of the offspring, and is possible to efficiently prepare wild type and mutated animals (FIG. 6).

The transgenic animal prepared as described above and its offspring exhibiting schizophrenic symptoms are useful in detecting a therapeutic effect on schizophrenia and screening for a therapeutic agent or agents for schizophrenia.

Example 5

Validation of Levels of STXBP1 in the Brain of Transgenic Mice: Immunofluorescence and Western Blotting Immunofluorescence was performed in 30 µm coronal adult brain free-floating sections of mice. Three different brain regions, cortex, striatum and hippocampus [Paxinos, 2003] were incubated with polyclonal rabbit anti-STXBP1 (Sigma) and polyclonal goat anti-EAAT3 (Santa Cruz Biotechnology) antibodies, followed by secondary staining for rabbit and mouse IgGs with highly cross-adsorbed AlexaFluor 594 and AlexaFluor 488, secondary antibodies (Invitrogen), respectively. Cellular nuclei were stained with the DNA-intercalating agent Hoechst. Preparations were examined using a Confocal Olympus Fluoview.

Figure 7:
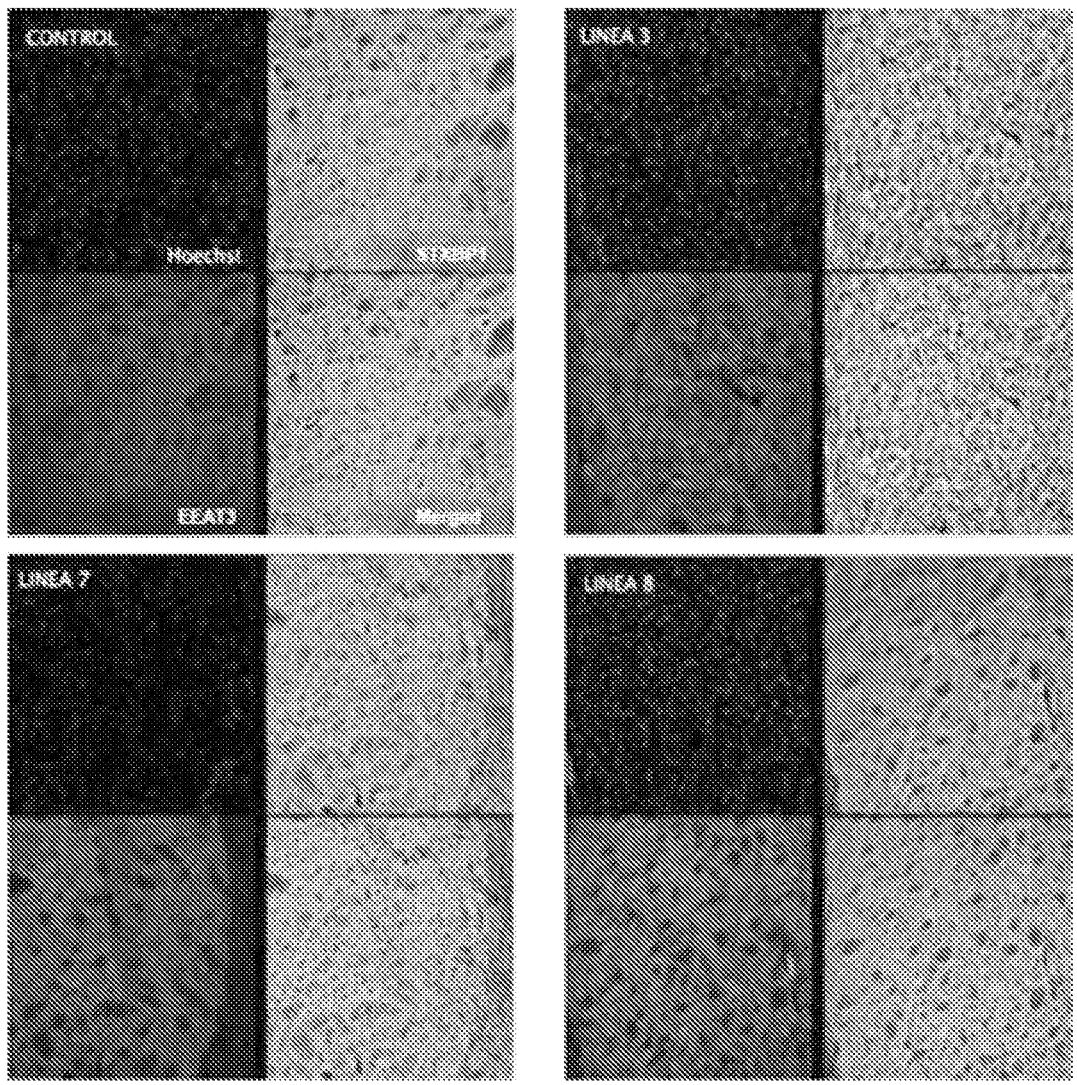
FIG. 7 shows immunofluorescence experiments in striatum region of the brain in control and in transgenic mice (L3, L7 and L8) for STXBP1, EAAT3, Hoetstch and merge.

These results showed an increase in the levels of STXBP1 in the three transgenic lines (L3, L7 and L8) and principally in striatum when compared with controls animals (FIG. 7).

The levels of STXBP1 protein in mouse cerebral cortex, striatum and cerebellum samples from control mice (wild type, n=4), transgenic mice from L3 (n=4), transgenic mice from L7 (n=4) and transgenic mice from line 8 (n=4) were validated by Western blotting with an antibody that specifically recognises the STXBP1 protein. The proteins were then extracted using the same extraction procedure as that used to prepare the bi-dimensional gels and in human samples. It was decided to measure the STXBP1 levels in both the cytosolic fraction and the non-cytosolic fraction for Western blot validation.

Briefly, 1 ml of lysis buffer (urea 7M; thiourea 2M; CHAPS 2%, D-Streak 0.2%, 20 µl of protease inhibitors) was added to 150 mg of cerebral cortex. Similarly 400 µl of lysis buffer was added to 40 mg of striatum region. Finally, 300 µl of lysis buffer was added to 30 mg of cerebellum. The mixture was sonicated in 20 second cycles for two minutes and then centrifuged at a speed of 75000 rpm for one hour at a temperature of 4° C. The supernatant was collected and the protein concentration determined using the Bradford test. The pellet was resuspended in 30 (cerebral cortex), 20 (striatum) or 10 (cerebellum) µl of lysis buffer and the quantity of protein determined by the Bradford method. Laemmli 5× buffer (Tris 0.5M pH 6.8, SDS 20% and bromophenol blue 0.01%) was added just prior to loading the sample onto the gel. Once the sample had been prepared, β-mercaptoethanol was added at a ratio of 1/7. The total protein concentration was adjusted to 1 µg/µl for all the samples from the cytosolic fraction and to 1 µg/µl for those from the non-cytosolic fraction. Once prepared, the sample was heated to 100° C. for five minutes and then centrifuged for 15 seconds at 4° C. Four micrograms of total protein per sample was loaded onto a 10% acrylamide gel for both the cytosolic and the non-cytosolic fractions. A minimum of two experiments were performed for each sample and the arithmetic mean of all the individual values was calculated.

Figure 8:
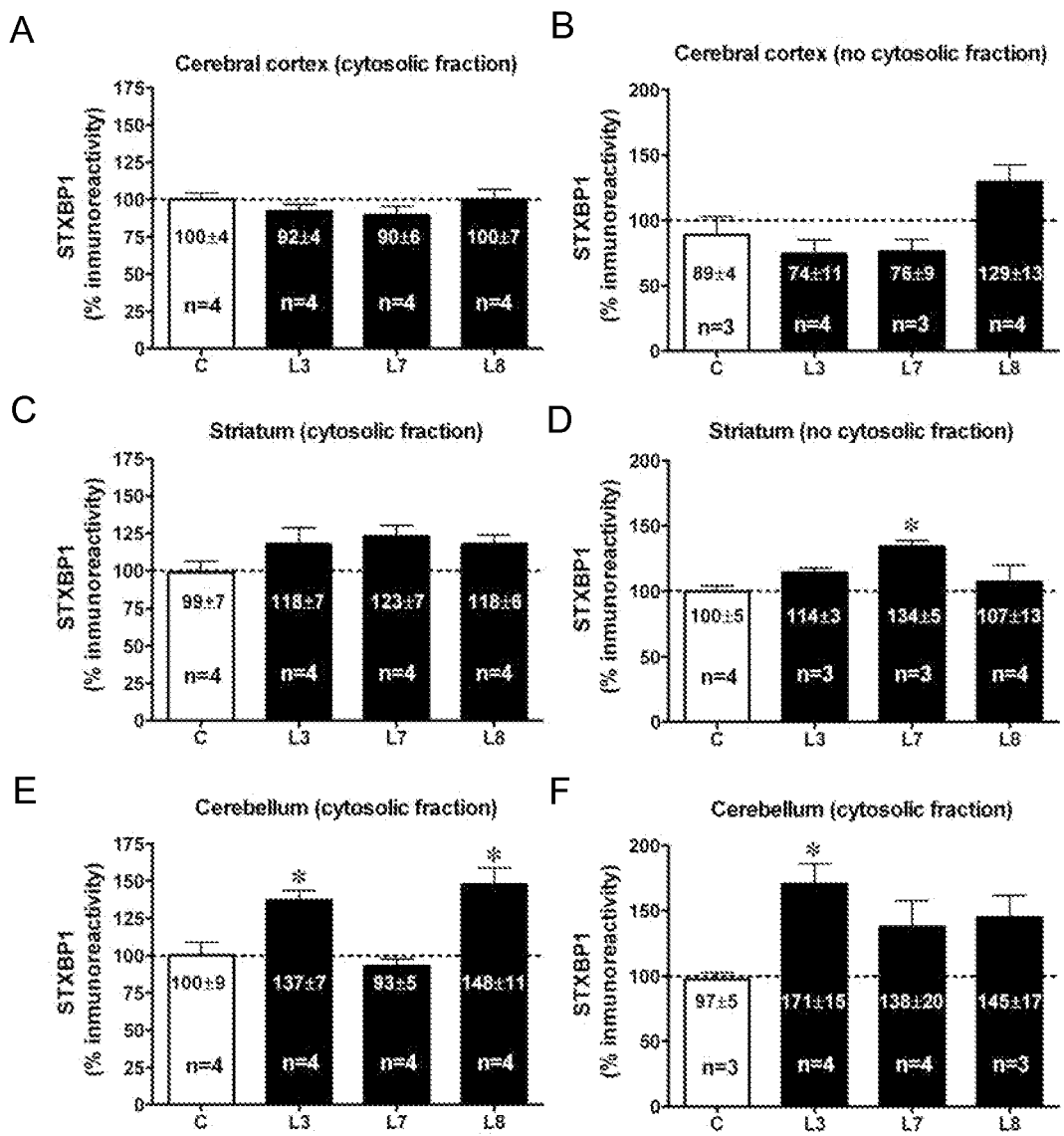
FIGS. 8A-8F show quantification of STXBP1. Immunoreactivity for the STXBP1 protein determined in (FIGS. 8A, 8C and 8E) the cytosolic fraction and (FIGS. 8B, 8D and 8F) non-cytosolic fraction of cerebral cortex, striatum (that include also thalamus and hypothalamus regions) and cerebellum (respectively) of wild type control mice and transgenic mice (L3, L7 and L8). The data are expressed as a percentage of the mean value±SEM (standard error) and expressed as percentage of control group. *p<0.05, when compared with the corresponding control group (the two-tailed one-sample t-test).

A significant increase in the levels of STXBP1 protein was observed in both the cytosolic and non-cytosolic fractions of striatum samples from L7 when compared with the levels of the same protein in control animals ($123\pm7$, n=4, p=0.06 and $134\pm5$, n=4, p=0.03 respectively). For the lines L3 and L8 there is also an increase of the STXBP1 levels but not significantly different from control animals (L3 cytosolic fraction $118\pm7$, n=4, p=0.06 and non-cytosolic fraction $114\pm3$, n=3, p=0.09; L8 cytosolic fraction $118\pm6$, n=4, p=0.09 and non-cytosolic fraction $107\pm13$, n=4, p=0.6). Furthermore, it was found that the expression of STXBP1 protein was much higher in the cerebellum of transgenic mice lines (L3, L7 and L8) compared with samples from the same brain region of control animals (L3 cytosolic fraction $137\pm7$, n=4, p=0.02 and non-cytosolic fraction $171\pm3$, n=4, p=0.01; L7 cytosolic fraction $93\pm5$, n=4, p=0.5 and non-cytosolic fraction $138\pm20$, n=4, p=0.2; L8 cytosolic fraction $148\pm11$, n=4, p=0.01 and non-cytosolic fraction $145\pm17$, n=4, p=0.05). Interestingly, it was found that the STXBP1 levels in transgenic mice lines (L3, L7 and L8) were similar to the control levels (L3 cytosolic fraction $92\pm4$, n=4, ns and non-cytosolic fraction $74\pm11$, n=4, ns; L7 cytosolic fraction $90\pm6$, n=4, ns and non-cytosolic fraction $76\pm9$, n=3, ns; L8 cytosolic fraction $100\pm7$, n=4, ns and non-cytosolic fraction $129\pm13$, n=4, ns) (FIG. 8). These results are similar that results obtained in using the immunofluorescence approach.

Example 6

Behavioural Testing

It is possible to detect whether or not a transgenic mouse shows schizophrenic symptoms by conventional methods of measuring schizophrenia-related disorders, such as the following methods described in items 1) to 4):

1) Motor Activity-Open Field Test

The open field consists of an opaque black walls square cage 25 cm×25 cm×25 cm (PanLab, Barcelona, Spain). The base of the cage consists of sensors able to detect horizontal movements of the mice. Testing was conducted in a silent room with constant light. Mice were individually placed in the centre of the apparatus to initiate a 10-min test session. To determine whether modification in the expression of STXBP1 alters the spontaneous motor activity, we compared transgenic and control mice in the open field for a period of 5 min. No differences were found between transgenic line 3 and wild-type animals. However, subtle changes were found when comparing transgenic lines 7 and 8 versus controls. The results revealed that distance in the open field significantly decreased in line 7 and line 8 (One-way ANOVA followed by Tukey test: $F(21,24)=14.42$; $p<0.05$) (FIG. 9A).

2) Rotarod Motor Coordination Test

Motor coordination was assessed by means of an automated rotarod apparatus (PanLab, Barcelona, Spain). A computer recorded the latency to fall in seconds. First, the mice were trained in the rotarod at a constant speed of 20 rpm until all the mice were able to spend at least 3 min. on the rod. Then, the mice were tested three consecutive times.

Figure 9:
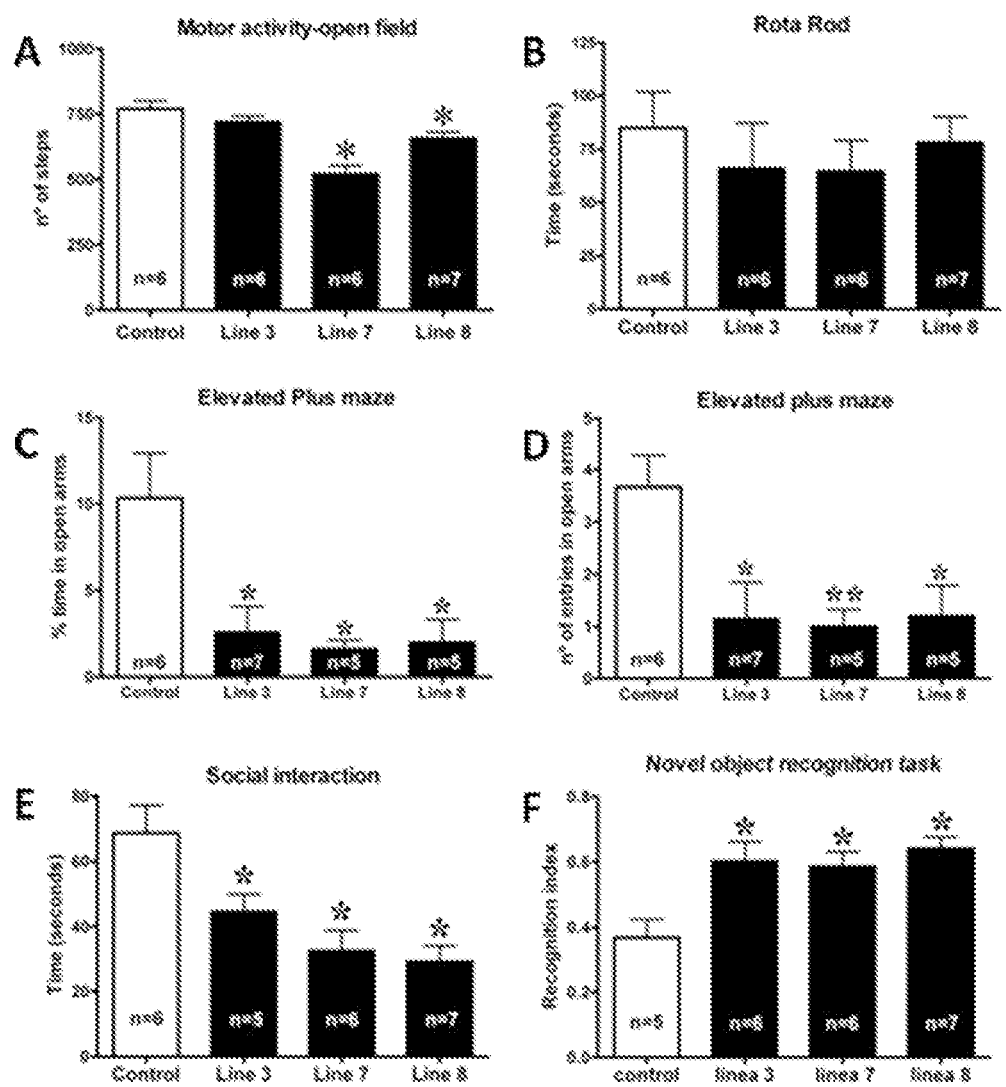
FIGS. 9A-9F show results of behavioural tests.

No significant differences were found between transgenic lines and wild-type animals in the Rotarod test (FIG. 9B). These results indicate that the impairments shown in the open-field test are not due to an impairment in the motility coordination of transgenic mice.

3) Assessment of Anxiety-Like Behaviours 3.1—Elevated Plus Maze

The elevated plus-maze is a commonly used test for measuring anxiety-like behaviour and innate fear in rodents [Crawley, 2000; Rogers and Cole, 1994]. The maze consists of two open (25 cm×5 cm) and two enclosed arms (25 cm×5 cm×30 cm), arranged such that the two arms of each type are opposite each other and extend from a central platform (5 cm×5 cm). The floor and side walls of the maze consist of opaque Plexiglass material. The maze is elevated to a height of 50 cm. Testing was performed in a dimly lit experimental room. Mice were individually introduced to the centre, the head facing the open arm. Behavioural parameters were recorded by a observer for 5 minutes. The percentage of each of the following parameters was measured: 1) open arms time 2) open arms entries. The maze was cleaned between sessions using 70% ethanol.

In the elevated plus maze, the percentage (%) of time spent in the open arms was significantly decreased in the three lines of transgenic mice (One-way ANOVA followed by a Tukey's Test $F(19,22)=5.476$, $p<0.006$) when compared with control animals (FIG. 8C). Similarly, the three lines of transgenic mice showed a significant decrease in the numbers of entries in the open arms (One-way ANOVA followed by a Tukey's Test $F(19,22)=4.469$, $p<0.02$) (FIG. 9D).

3.2—Social Interaction

When two mice from separate cages are placed together in a small chamber in which neither has established territory, they engage in social interaction which includes a variety of behavioural patterns: sniffing, following, grooming, kicking, crawling under or over the partner, and touching or nearly touching of faces.

On the day of the experiment, pairs of mice from different home cages were placed together in a small plastic cage (20 cm×40 cm×10 cm) with a cardboard lid and fresh wood litter on the floor (no change in the light level). The time that mice socially interacted was measured for 5 min.

In the social interaction test, the time in which mice from separate cages (unfamiliar situation) engaged in social interaction was significantly lower ($p<0.001$) in transgenic mice (One Way ANOVA followed by Tukey's Test F(20,23)=8.026 p<0.05) when compared with controls animals (FIG. 9E).

4) Novel Object Recognition Task (NORT)

The NORT was conducted in an transparent Plexiglas arena (35 cm×45.5 cm×36 cm) with objects that could not be displaced by the mice. Adult male mice were habituated to the arena, in the absence of objects, for 30 min. on each of 3 successive days prior to the test day. On the test day, the mice were habituated to the arena for 1 min. and then two different objects were placed in the cage in two adjacent corners (7.5 cm from each wall). During the sample phase, each mouse was placed in the centre of the arena, and the time it spent exploring each object was recorded over a 5-min. period with stopwatches. The next day, the mouse was returned to the arena for the choice phase, with one object from the sample phase (familiar object) and a novel object. Individuals unaware of the treatment conditions or the mouse's genotype recorded the time the mouse spent exploring each object over a 3-min. period using stopwatches. Exploration was defined as directing the nose toward the object at a distance of less than 1 cm and included placing one or more paws on the object. The total time spent investigating both objects in the sample phase was recorded and compared among the three mouse genotypes. In the choice phase, the proportion of time the mouse spent with the novel object was determined by subtracting the time spent with the familiar object from that spent with the novel object and dividing this time by the total time spent exploring both objects. The resultant value was a discrimination ratio, whereby a value of 0 indicated that equal time was spent investigating both objects and a value of 1 indicated that all time was spent investigating the novel object.

In the NORT, the recognition index significantly increased in the three lines of transgenic mice, 3, 7 and 8, (One-way ANOVA followed by a Tukey's Test F(20,23)=5.927; p<0.05 for line 3 and 7 and p<0.001 for line 8) when compared with their controls (FIG. 9F). This increase in the recognition index is believed to be due to an increase in the stress response of the animal due to presence of a new object.

The transgenic mouse line in accordance with the invention was compared with wild-type mice in a range of behavioural tests. The results are described in Table 2 below.

TABLE 2

Results of behavioural testing

| Test | Results |
|---|---|
| Open field | The open field test is designed to measure behavioral responses such as locomotor activity, hyperactivity, and exploratory behaviors. The open field test is also used as a measure of anxiety. In our experiments the transgenic mice spent less time in the centre of the open field when compared with the wild type group, this behaviour is associated with anxiety-like responses. This phenotype is considered to reflect a decreased motivation on the part of the transgenic animals to explore, which might be related to the negative symptoms of schizophrenia (decreased motivation, and social withdrawal) and has been observed in other animal models [Hattori et al., 2008]. |
| Elevated plus maze | The transgenic mice showed an increase in the time spent in the closed arms of the elevated plus maze (EPM) in comparison to the wild type group. The behaviour observed in the EPM test followed the same trend as the results obtained with the open field experiments. This behaviour is considered an anxiety-like |

TABLE 2-continued

Results of behavioural testing

| Test | Results |
|---|---|
| | response with similarities to the negative symptoms observed in schizophrenia [Hattori et al., 2008] |
| Pre-pulse inhibition | The transgenic mice showed a reduced pre-pulse inhibition (PPI) response when compared to the control group. There have been numerous reports of a deficiency in the PPI response in schizophrenia patients, a reduced PPI response has been suggested to meet the criteria as an endophenotype for genetic studies of schizophrenia [Powell et al., 2009]. |
| Fear conditioning | The transgenic mice showed a reduction in the percentage of time spent in a freezing response when compared with the control group. The result suggests that the transgenic animals exhibit an altered fear memory. This feature has been described in other animal models of schizophrenia and belongs to the group of cognitive symptoms observed in schizophrenia [Bhardwaj et al., 2009]. |
| Social interaction | In the social interaction test the transgenic mice showed a significant decrease in the number of social contacts compared with wild-type mice. Reduced social interaction is a common behavioural phenotype present in schizophrenia correlating with other negative symptoms [Koike et al., 2009]. |
| Novel object recognition | In this test the mice were found to have a reduction in their short term memory. The time spent in the presence of novel objects presented to the transgenic group related to their total exploration time is reduced when compared to the wild type group. Deficiencies in short term memory are considered among the cognitive symptoms associated with schizophrenia and has been observed in other animal models of the disease [McLean et al., 2009]. |

Example 7

Method of Screening Agents as Potential Schizophrenia Therapeutics

A potential therapeutic agent for the treatment of schizophrenia can be tested by administering the test substance to a transgenic animal of the invention. Following the administration of the substance, the behavioural tests (for example behavioural tests as disclosed in Example 6 above) are repeated, in order to evaluate whether the compound modifies the results observed prior to administration of the compound. Preferably, the one or more behavioural tests are additionally performed on one or more untreated transgenic animals of the invention to act as controls.

A potential therapeutic agent may be classified as a candidate for further investigation on the basis of a positive screening result. A positive screening result may be one in which the test agent is found to restore or normalise a behavioural outcome of an animal of the invention to or towards the behavioural outcome of a normal animal (e.g. an animal not having altered levels of STXBP1 but otherwise identical to the animal of the invention). In some cases, the behavioural outcome may be quantified and the degree of restoration or normalisation of the behavioural outcome measured. In this way a pre-determined threshold level may be set to allow classification of an agent being screened as positive or negative for restoration or normalisation of behaviour. Agents classified as positive in this way may then be subjected to further animal testing and/or human clinical testing for safety and/or efficacy in the treatment of a psychiatric illness, e.g. schizophrenia.

The substances which can used for the screening method are not limited, but may include for example: commercially available compounds, various known compounds registered in compound databases, compounds obtained by combinatorial chemical files, compounds obtained by combinatorial chemistry techniques, or chemically or biologically modified compounds derived from other compounds, culture supernatants of microorganisms, natural components derived from plants or marine organisms, animal tissue, interference RNA, peptides and antibodies. Preferably, the agent is a compound capable of passing through the blood-brain barrier (BBB) such that it is "centrally active".

Preferably, one or more positive control compounds, which are known to have therapeutic activity in the treatment of psychiatric illness, particularly schizophrenia, are used in the screening method as a reference against which to compare the effects of any test agent. Preferred positive control compounds include atypical antipsychotics such as: Clozapine, Risperidone, Olanzapine, Quetiapine, Ziprasidone, Aripiprazole, Paliperidone, Asenapine, Iloperidone, Sertindole, Zotepine, Amisulpride, Bifeprunox and Melperone and typical antipsychotics such as: Chlorpromazine, Fluphenazine, Haloperidol, Molindone, Thiothixene, Thioridazine, Trifluoperazine, Loxapine, Perphenazine, Prochlorperazine, Pimozide and Zuclopenthixol.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

REFERENCES

1. Arguello & Gogos, 2006, Neuron, 52(1): 179-196.
2. Behan et al., 2008, Molecular Psychiatry, E-publication, 12 Feb. 2008, doi:10.1038/mp.2008.7
3. Crawley et al., 2000, *What's Wrong with My Mouse? Behavioral Phenotyping of Transgenic and Knockout Mice* (Wiley, New York).
4. Ellenbroek & Cools, 2000, Behav Pharmacol. 11(3-4): 223-233.
5. Fatemi et al., 2001, Neuroreport, 12:3257-3262.
6. Geyer & Moghaddam, 2002, Neuropsychopharmacology: The Fifth Generation of Progress, (eds. K. L. Davis, D. Charney, J. T. Coyle, & C. Nemeroff), Lippincott Williams & Wilkins, Chapter 50, pp 689-701.
7. Gray et al., 2006, Neurosci Lett, 391:112-115.
8. Halim et al., 2003, Mol Psychiatry, 8:797-810.
9. Honer et al., 2002, Cerebral Cortex, 12:349-356.
10. Imai et al., 2001, Neurosci Lett, 305:185-188.
11. Mukaetova-Landiska et al., 2002, Neurosci Lett, 317: 161-165.
12. Rogers and Cole, 1994, Eur J. Pharmacol. 22; 261(3):321-5.
13. Rossler et al., 2005, Eur Neuropsychopharmacol, 15:399-409.
14. Sollner et al., 1993a, Cell 75:409-418.
15. Sollner et al., 1993b, Nature 362:318-324.
16. Thompson et al., 2003, Biol Psychiatry, 53:1132-1137.
17. Verhage et al., 2000, Science, 287:864-869.
18. Vercauteren et al., 2007, Proteomics, 7: 3569-3579.
19. Voets et al, 2001, Neuron, 31: 581-591.
20. Weinberger, 2005, Clin Ther. 27: Suppl. A: S8-S15.
21. Young et al., 1998, Cereb Cortex, 8:261-268.
22. Bracher and Weissenhorn, 2001, J Mol Biol, 306(1): 7-13.
23. Bhardwaj S K, Baharnoori M, Sharif-Askari B, Kamath A, Williams S and Srivastava L K (2009) Behavioral Characterization of Dysbindin-1 Deficient Sandy Mice. *Behav Brain Res* 197:435-441.
24. Hattori S, Murotani T, Matsuzaki S, Ishizuka T, Kumamoto N, Takeda M, Tohyama M, Yamatodani A, Kunugi H and Hashimoto R (2008) Behavioral Abnormalities and Dopamine Reductions in Sdy Mutant Mice With a Deletion in Dtnbp1, a Susceptibility Gene for Schizophrenia. *Biochem Biophys Res Commun* 373:298-302.
25. Koike H, Ibi D, Mizoguchi H, Nagai T, Nitta A, Takuma K, Nabeshima T, Yoneda Y and Yamada K (2009) Behavioral Abnormality and Pharmacologic Response in Social Isolation-Reared Mice. *Behav Brain Res* 202:114-121.
26. McLean S L, Idris N F, Woolley M L and Neill J C (2009) D(1)-Like Receptor Activation Improves PCP-Induced Cognitive Deficits in Animal Models: Implications for Mechanisms of Improved Cognitive Function in Schizophrenia. *Eur Neuropsychopharmacol* 19:440-450.
27. Powell S B, Zhou X and Geyer M A (2009) Prepulse Inhibition and Genetic Mouse Models of Schizophrenia. *Behav Brain Res*. May 3 [Epub ahead of print]; PMID: 19397931.

The invention claimed is:

1. A transgenic mouse whose genome comprises a polynucleotide encoding a syntaxin-binding protein 1 (STXBP1) polypeptide having at least 90% sequence identity with SEQ ID NO: 2 operably linked to an excitatory amino acid transporter 3 (EAAT3) promoter, wherein said transgenic mouse has greater than wild-type expression of the STXBP1 polypeptide in at least its brain cortex, and wherein the transgenic mouse exhibits one or more behaviours selected from the group consisting of reduced motor activity in an open field test, reduced time spent in open arms of an elevated plus maze, reduced social interaction, increased recognition index in a novel object recognition task, and decreased prepulse inhibition of startle response.

2. The transgenic mouse according to claim 1, wherein said polynucleotide is present in a higher than wild-type copy number.

3. The transgenic mouse according to claim 1, wherein said polynucleotide encodes an STXBP1 polypeptide having the amino acid sequence of SEQ ID NO: 2.

4. The transgenic mouse according to claim 1, wherein the EAAT3 promoter comprises a polynucleotide having at least 80% nucleic acid sequence identity to the sequence of SEQ ID NO: 6 or a polynucleotide having the sequence of SEQ ID NO: 6.

5. The transgenic mouse according to claim 1, having at least 10% greater expression of the STXBP1 polypeptide in said at least brain cortex, as measured by Western blot, immunofluorescence or qPCR of an STXBP1 mRNA.

6. A method of producing the transgenic mouse of claim 1, comprising:
   introducing a vector comprising a polynucleotide encoding a syntaxin-binding protein 1 (STXBP1) polypeptide having at least 90% sequence identity with SEQ ID NO: 2 operably linked to an excitatory amino acid transporter 3 (EAAT3) promoter and optionally further regulatory sequences into one or more cells of the mouse at an embryonic stage, such that the transgenic mouse of claim 1 is obtained.

7. The method of claim 6, wherein the EAAT3 promoter comprises a polynucleotide having at least 80% nucleic acid sequence identity to the sequence of SEQ ID NO: 6 or a polynucleotide having the sequence of SEQ ID NO: 6.

8. The method according to claim 6, wherein said polynucleotide encodes
   an STXBP1 polypeptide having the amino acid sequence of SEQ ID NO: 2.

9. The method of claim 6, further comprising extracting DNA from the mouse to confirm the incorporation of the polynucleotide into the genome of the mouse.

10. An in vivo method for identifying an agent that reduces the presence or severity of one or more behaviours in a mouse, said one or more behaviours being selected from the group consisting of reduced motor activity in an open field test, reduced time spent in open arms of an elevated plus maze, reduced social interaction, increased recognition index in a novel object recognition task, and decreased prepulse inhibition of startle response, the method comprising:
   a) administering a test agent to the transgenic mouse of claim 1; and
   b) subsequently assessing the presence or severity of said one or more behaviours;
   wherein a reduction in said one or more behaviours relative to the same one or more behaviours in a control transgenic mouse of claim 1 that has not been administered the test agent indicates that the test agent reduces the presence or severity of the one or more behaviours in the mouse.

\* \* \* \* \*

```
SEQUENCE LISTING

<160> NUMBER OF SEQ ID NOS: 8

<210> SEQ ID NO 1
<211> LENGTH: 3617
<212> TYPE: DNA
<213> ORGANISM: Mus musculus

<400> SEQUENCE: 1
gcggggcgcg cggcccgggg gaggcgacgg tgtcgcggga ggagcatcgg agcccgaaga      60
ctcgaagaac gccatggccc ccattggcct caaggcggtg gtcggagaga agatcatgca     120
tgatgtgatc aagaaggtga agaagaaggg cgagtggaag gtgctggtgg tggaccagtt     180
aagcatgagg atgctgtcct cctgctgcaa gatgacagac atcatgaccg agggcatcac     240
```

```
aattgtggag gatatcaaca agcgccgaga gccactcccc agcctggagg ccgtgtacct    300
catcacccca tctgagaagt ctgtccactc tctgatcagt gattttaagg acccgccgac    360
tgctaaatat cgggctgcgc atgtgttctt cacagactcg tgtccagatg ccctatttaa    420
cgagctggta aaatcccgag cagccaaagt catcaagacg ctgacggaaa tcaacattgc    480
gtttctcccc tatgagtccc aggtgtattc cctggactcc gctgactctt ccaaagctt     540
ctacagccct cacaaggcgc agatgaagaa tccgatactg gaacgcctgg cagagcagat    600
cgcaaccctg tgtgccaccc tgaaggagta tccagctgtg cggtatcggg gggagtacaa    660
ggacaatgcc ttgctggctc agctgatcca ggacaagctg gatgcctata aagccgacga    720
tccaacaatg ggggagggtc ccgacaaggc acggtcccag ctcctgatcc tggatcgtgg    780
ctttgacccc agctcccctg tgctccatga actgacattc caggctatga gttatgacct    840
gctgcctatc gaaaatgatg tttacaagta tgagaccagc ggcattggag aggcgcgggt    900
gaaggaggtg ctactggatg aggacgatga cctgtggatt gcgctgcgac acaagcacat    960
cgcagaggtg tcccaggaag tcacccggtc tctgaaggac ttttcctcta gcaagaggat    1020
gaacactggc gagaagacca ccatgcggga cctgtcccag atgctgaaga aaatgcccca    1080
gtaccagaag gagctcagca gtattcgact tcacctgcac cttgctgaag actgcatgaa    1140
gcattaccaa ggcactgtag acaaaactctg ccgcgtggag caggacctgg caatgggcac    1200
agatgctgag ggggaaaaaa tcaaggaccc catgagagcc attgtcccca tcctgctgga    1260
tgcgaacgtc agcacttacg acaaaatccg tatcatcctt ctctacatct tcctgaagaa    1320
cggtatcact gaggagaacc taaacaaact catccagcac gctcagatac ccccagagga    1380
cagcgagatc atcaccaaca tggctcacct cggcgtgccc atcgtcacgg attccacact    1440
acgccgccga agcaaaccgg agcggaagga gcgtatcagt gagcagacct accagctctc    1500
acgatggacc ccgatcatta agacattat ggaggacact atcgaagaca agctggatac     1560
aaagcactac ccatacatct ctacccgctc gtccgcgtcc ttcagcacca ctgctgtgag    1620
tgcccgctat ggacattggc acaagaataa ggccccggg gagtaccgca gcggtcccccg     1680
cctcattatt ttcatccttg ggggtgtgag cctgaatgag atgcgctgtg cttacgaagt    1740
gacccaggcc aacggcaagt gggaagtgct gataggttct actcacattc tcactcccac    1800
caaattcctc atgacctga gacaccccga cttcaggag tcctctaggg tatcttttga      1860
ggatcaggct ccaacaatgg agtgagagcc aaagagacaa agatccacgc acattctcac    1920
cccacagaaa ctgctggaca cgctgaagaa gctgaataaa acagatgaag aaataagcag    1980
ttaaaaaata agctgccccc caaaaccccg gctcccttcc caaaatgctc tgcagctccc    2040
ccgtgcgcca cctcggttac tctgctgcct cccccagccct gcacgccctg ccacccccgt    2100
tgccgtgctg agttcttctc ctgtgcgatg acaccccatc ttgtcctctg aaaagcaaga    2160
gagtaatgtg ttgttttta aaaatgagca tcttctgtat gtatcccaca gtaagttcac     2220
atgcaagctc cacactgcag aagcgtcaga actccggacc gagtgaattc tcccttattt    2280
atgaccccgt gacctgtata tagccctgtc ccgcgtgtgc acattgcttg aatatggaaa    2340
ggtagatgtg tgggtgtctc tccaagcttg gttggattca tttctgtcct tgttggtgtt    2400
tgttccccgg ataggacatg ctgagggagt gatgttctcg ctagcccctg ctcgctccct    2460
gttctcagcg atgagcagac acctctggag gctggcgtgg aacgagcctc ctctttgcac    2520
ctatggggga ggcttagggt gtccacagga agccagtctg agtgccggcc agtgtggtct    2580
```

```
ccagagcctg gcactgcttt ccctgatctg tgtccatact gttgtaacaa gttaagccct    2640
tcaggctaaa tcagcctgcc tagtgccctc ggagcctcca gagttaggtc tgaccagccc    2700
cctgcttgaa cacagtttgg atagaggcca agggtcaggg gtgggctgga agctgtgagt    2760
ttggcactct ggtcaagggt gctttgctgt aggagctagg cctgaagaat gggggccctg    2820
ctgcttagtc agagtcccct cagtttaaga tacttcatca atcttaagtt tgtgtagtgt    2880
acagtcatgt gtcattgtgg ttgtatgaaa aggatcattt tattctttgt attagtcatc    2940
actgtataaa acatagctag ctataaagca gaaattccag aagccgatgc tggaaggatg    3000
gtctccaccc tcaggacgca gcagccccct gagcatgctg ctcaccctgc tgctgtagtc    3060
gtgaaacaaa gacagtggaa gtcacaaaaa tgtccccagc ccagtccccg ccctcccctc    3120
ccgcagattt gtacgtatta ctgtgtctcg tgctgtcttc gcaaacgtgg tgtacgcctg    3180
ccgcaggtgt cctgtgccct tctccctccc tgactctaga gtctctcttc tccttagttc    3240
tcaggcctct cccctgctcc tctccagtga acctttccc ttaggactga accacactag    3300
caccggttga tttcttctgt agcgcttctc ccatcccttc ctccggtcaa gcaatgctca    3360
tgcttcagga tcttgtttgt cgaacatgtg gggtttcctt tatgttattt atataaataa    3420
tttctcaaat ggatatttaa aaaaaagcta gtctgtcttg aaacttgtta acttgaaact    3480
cttgaatctc agtgtttaaa gtatggaagc acaaccgtgt accgctctgt accgtcctgt    3540
actgcagcat ttgagtctaa taagacgtc agctctcaaa aaaaaaaaa aaaaaaaaa     3600 aaaaaaaaaa aaaaaaa                                                  3617
```

<210> SEQ ID NO 2
<211> LENGTH: 599
<212> TYPE: PRT
<213> ORGANISM: Mus musculus

<400> SEQUENCE: 2

```
Met Ala Pro Ile Gly Leu Lys Ala Val Gly Glu Lys Ile Met His
1               5                   10                  15

Asp Val Ile Lys Lys Val Lys Lys Gly Glu Trp Lys Val Leu Val
                20                  25                  30

Val Asp Gln Leu Ser Met Arg Met Leu Ser Ser Cys Cys Lys Met Thr
            35                  40                  45

Asp Ile Met Thr Glu Gly Ile Thr Ile Val Glu Asp Ile Asn Lys Arg
        50                  55                  60

Arg Glu Pro Leu Pro Ser Leu Glu Ala Val Tyr Leu Ile Thr Pro Ser
65                  70                  75                  80

Glu Lys Ser Val His Ser Leu Ile Ser Asp Phe Lys Asp Pro Thr
                85                  90                  95

Ala Lys Tyr Arg Ala Ala His Val Phe Phe Thr Asp Ser Cys Pro Asp
            100                 105                 110

Ala Leu Phe Asn Glu Leu Val Lys Ser Arg Ala Lys Val Ile Thr
        115                 120                 125

Leu Thr Glu Ile Asn Ile Ala Phe Leu Pro Tyr Glu Ser Gln Val Tyr
        130                 135                 140

Ser Leu Asp Ser Ala Asp Ser Phe Gln Ser Phe Tyr Ser Pro His Lys
145                 150                 155                 160

Ala Gln Met Lys Asn Pro Ile Leu Glu Arg Leu Ala Glu Gln Ile Ala
                165                 170                 175

Thr Leu Cys Ala Thr Leu Lys Glu Tyr Pro Ala Val Arg Tyr Arg Gly
            180                 185                 190
```

```
Glu Tyr Lys Asp Asn Ala Leu Leu Ala Gln Leu Ile Gln Asp Lys Leu
        195                 200                 205

Asp Ala Tyr Lys Ala Asp Pro Thr Met Gly Glu Gly Pro Asp Lys
210                 215                 220

Ala Arg Ser Gln Leu Leu Ile Leu Asp Arg Gly Phe Asp Pro Ser Ser
225                 230                 235                 240

Pro Val Leu His Glu Leu Thr Phe Gln Ala Met Ser Tyr Asp Leu Pro
                245                 250                 255

Ile Glu Asn Asp Val Tyr Lys Tyr Glu Thr Ser Gly Ile Gly Glu Ala
                260                 265                 270

Arg Val Lys Glu Val Leu Leu Asp Glu Asp Asp Leu Trp Ile Ala
                275                 280                 285

Leu Arg His Lys His Ile Ala Glu Val Ser Gln Glu Val Thr Arg Ser
        290                 295                 300

Leu Lys Asp Phe Ser Ser Lys Arg Met Asn Thr Gly Glu Lys Thr
305                 310                 315                 320

Thr Met Arg Asp Leu Ser Gln Met Leu Lys Met Pro Gln Tyr Gln
                325                 330                 335

Lys Glu Leu Ser Lys Tyr Ser Thr His Leu His Leu Ala Glu Asp Cys
                340                 345                 350

Met Lys His Tyr Gln Gly Thr Val Asp Lys Leu Cys Arg Val Glu Gln
                355                 360                 365

Asp Leu Ala Met Gly Thr Asp Ala Glu Gly Glu Lys Ile Asp Pro Met
        370                 375                 380

Arg Ala Ile Val Pro Ile Leu Leu Asp Ala Asn Val Ser Thr Tyr Asp
385                 390                 395                 400

Lys Ile Arg Ile Ile Leu Leu Tyr Ile Phe Leu Lys Asn Gly Ile Thr
                405                 410                 415

Glu Glu Asn Leu Asn Lys Leu Ile Gln His Ala Gln Ile Pro Pro Glu
                420                 425                 430

Asp Ser Glu Ile Ile Thr Asn Met Ala His Leu Gly Val Pro Ile Val
        435                 440                 445

Thr Asp Ser Thr Leu Arg Arg Arg Ser Lys Pro Glu Arg Lys Glu Arg
450                 455                 460

Ile Ser Glu Gln Thr Tyr Gln Leu Ser Arg Trp Thr Pro Ile Ile Lys
465                 470                 475                 480

Asp Ile Met Glu Asp Thr Ile Glu Asp Lys Leu Asp Thr Lys His Tyr
                485                 490                 495

Pro Tyr Ile Ser Thr Arg Ser Ser Ala Ser Phe Ser Thr Ala Val Ser
                500                 505                 510

Ala Arg Tyr Gly His Trp His Lys Asn Lys Ala Pro Gly Glu Tyr Arg
                515                 520                 525

Ser Gly Pro Arg Leu Ile Ile Phe Ile Leu Gly Gly Val Ser Leu Asn
        530                 535                 540

Glu Met Arg Cys Ala Tyr Glu Val Thr Gln Ala Asn Gly Lys Trp Glu
545                 550                 555                 560

Val Leu Ile Gly Ser Thr His Ile Leu Thr Pro Thr Lys Phe Leu Met
                565                 570                 575

Asp Leu Arg His Pro Asp Phe Arg Glu Ser Ser Arg Val Ser Phe Glu
                580                 585                 590

Asp Gln Ala Pro Thr Met Glu
                595
```

<210> SEQ ID NO 3
<211> LENGTH: 3899
<212> TYPE: DNA
<213> ORGANISM: Homo sapiens

<400> SEQUENCE: 3

```
ctgacgcgcg gctgcggggc ggagagctgc ggctggccca gcgcgcccac ctgaggaggc      60
ggcggggtcc gcaggcgtcg cgggacgagg agatcggagc cgggagactc gcgcagcgcc     120
atggccccca ttggcctcaa agctgttgtc ggagagaaga ttatgcatga tgtgataaag     180
aaggtcaaga agaaggggga atggaaggtg ctggtggtgg atcagttaag catgaggatg     240
ctgtcctcct gctgcaagat gacagacatc atgaccgagg cataacgat tgtggaagat     300 atcaataagc gcagagagcc gctccccagc ctggaggctg tgtatctcat cactccatcc     360
gagaagtccg tccactctct catcagtgac tttaaggacc cgccgactgc taaataccgg     420
gctgcacacg tcttcttcac tgactcttgt ccagatgccc tgtttaatga actggtaaaa     480
tcccgagcag ccaaagtcat caaaactctg acggaaatca atattgcatt ctcccgtat    540 gaatcccagg tctattcctt ggactctgct gactcttcc aaagcttcta cagtccccac     600
aaggctcaga tgaagaatcc tatactggag cgcctggcag agcagatcgc gacccttgt    660 gccaccctga aggagtaccc ggctgtgcgg tatcgggggg aatacaagga caatgccctg     720
ctggctcagc taatccagga caagctcgat gcctataaag ctgatgatcc aacaatgggg     780
gagggcccag acaaggcacg ctcccagctc ctgatcctgg atcgaggctt tgaccccagc     840
tcccctgtgc tccatgaatt gacttttcag gctatgagtt atgatctgct gcctatcgaa     900
aatgatgtat acaagtatga ccagcggc atcggggagg cacgggtgaa ggaggtgctc      960
ctggacgagg acgacgacct gtggatagca ctgcgccaca gcacatcgc agaggtgtcc    1020 caggaagtca cccggtctct gaaagatttt tcttctagca agagaatgaa tactggagag    1080
aagaccacca tgcgggacct gtcccagatg ctgaagaaga tgcctcagta ccagaaagag    1140
ctcagcaagt actccacccca cctgcacctt gctgaggact gtatgaagca ttaccaaggc    1200
accgtagaca aactctgccg agtggagcag gacctggcca tgggcacaga tgctgaggga    1260
gagaagatca aggaccctat gcgagccatc gtccccattc tgctggatgc caatgtcagc    1320
acttatgaca aaatccgcat catccttctc tacatctttt tgaagaatgg catcacggag    1380
gaaaacctga acaaactgat ccagcacgcc cagatacccc cggaggatag tgagatcatc    1440
accaacatgg ctcacctcgg cgtgcccatc gtcaccgatt ccacgctgcg tcgccggagc    1500
aagccggagc ggaaggaacg catcagcgag cagacctacc agctctcacg gtggactccg    1560
attatcaagg acatcatgga ggacactatt gaggacaaac ttgacaccaa acactaccct    1620
tatatctcta cccgttcctc tgcctccttc agcaccaccg ccgtcagcgc ccgctatggg    1680
cactggcata agaacaaggc cccaggcgag taccgcagtg gccccgcct catcattttc    1740 atccttgggg gtgtgagcct gaatgagatg cgctgcgcct acgaggtgac ccaggccaac    1800
ggaaagtggg aggtgctgat aggttctact cacattctta ctcccaccaa atttctcatg    1860
gacctgagac accccgactt cagggagtcc tctagggtat cttttgagga tcaggctcca    1920
acaatggagt gagagccaaa gaaacaaaga tccacacaca tcctcaccc acagaaactg    1980 ctggacacac tgaagaaact gaataaaca gatgaagaaa taagcagtta aaaaaataag    2040
tcgcccctcc aaaacacgcc cccatcccac agcgctccgc agcttccac caccgcccgc    2100 ctcagttcct ttgcgtctgt tgcctcccca gccctgcacg ccctggctgg cactgttgcc    2160
```

```
gctgcattct cgtgttcagt gatgccctct tcttgtttga acaaaagaa ataatgcat    2220 tgtgttttt aaaagagta tcttatacat gtatcctaaa aagagaagct catgtgcaat    2280
tggtgcacag caggagaaat ttctggactg ttaggatgaa tggacgcctt ctccccgtta   2340
tttaagattt gtgaccttgt acataaccct gggtgacgtg cacattgctt gggtatggaa   2400
cggtagaaat ttgggtgttt ttaaaacctt gtttggggtt gttcctgtcc ttgttgagaa   2460
tcatagagat gtctgtgttc ttggagtatt tcacactgag gactaatctg ctatcttcat   2520
tccagtccct acccctcagt gcctgctctc atccaaataa cctgggaggt gacaatcagg   2580
atatctcagg aggtccaagg tggaacagac ctctttgcct ttcccagcgt ctcataccc    2640 cggtagtgca gctgtgggtg gaggctgggg tgtctgcacg aagtcaggcc agcgtcctcc   2700
tccacagcct gtcactgccc cctccccagc ctgtgtccac agtgctgtga tcccgaggga   2760
agtcctccag tctaagtcac agtgccctga caggtgagaa gcaaactccc gctggaagcc   2820
tccatctctt tggaaaaaca gttagtctgg agcctgtggc ccaggccctt ctgtccccag   2880
gcatcatccc aacagctcat tttccctagt ccgccttcgt tcaagggtca ggaatggacc   2940
agaacagatg ggttctggag gcccctgaac agagggctat ggctgtggag aaggttcttg   3000
gcccgttgga ctcacacaga ccctgtaccc tctcggcaag catcttcagt cagattatcc   3060
tcagtttcag atacttcata ataccttgtg ttgtgtgggg tcatacatca tcgtgtttgt   3120
aagagaagat ggtcatttta ttctctgtat aaaacttagc tctaaagcag aaactaaagc   3180
agcaaatgca ggaaggctgt ctcgccatcc tcaagactca gcagctctca ttctccagtg   3240
gtgagcacac catttgtgct gctgctgttg tcgtgaaata taataacagt ggaagtcaca   3300
aaaatgtccc ctgcccagcc ccctcgccgc ccttgacctc ctgcaggcca tgtgtgtatt   3360
acttgtctag tgatgtcctc tcaaagtgct gtacgcgagc tcggcgccac ctccgcctcc   3420
ctttcagagc ctgctccccg ccctctctgc tcgctgcatt gtggtgttct cttctcaagg   3480
ctttgaaatc tccccttgca ctgagattag tcgtcagatc tctccccgtc tccctcccaa   3540
cttatacgac ctgatttcct taggacggaa ccgcaggcac ctgcgccggg cgtcttactc   3600
ccgctgcttg ttctgtcccc tccctcggac caaacagtgc tcatgcttca ggaccttgtt   3660
tgtcgaagat gttggtttcc cttctctgt tatttatata aaaataattt atcaaaagga    3720 tatttttaaaa aagctagtct gtcttgaaac ttgtttacct taaaattatc agaatctcag   3780
tgtttgaaag tactgaagca caaacatata tcatctctgt accattctgt actaaagcac   3840
ttgagtctaa taaataaaga aatcagcacc ccttcccggt gtccaggggg aaaaaaaaa    3899
```

<210> SEQ ID NO 4
<211> LENGTH: 594
<212> TYPE: PRT
<213> ORGANISM: Homo sapiens

<400> SEQUENCE: 4

```
Met Ala Pro Ile Gly Leu Lys Ala Val Val Gly Glu Lys Ile Met His
1               5                   10                  15

Asp Val Ile Lys Lys Val Lys Lys Lys Gly Glu Trp Lys Val Leu Val
                20                  25                  30

Val Asp Gln Leu Ser Met Arg Met Leu Ser Ser Cys Cys Lys Met Thr
            35                  40                  45

Asp Ile Met Thr Glu Gly Ile Thr Ile Val Glu Asp Ile Asn Lys Arg
        50                  55                  60
```

```
Arg Glu Pro Leu Pro Ser Leu Glu Ala Val Tyr Leu Ile Thr Pro Ser
 65              70                  75                  80

Glu Lys Ser Val His Ser Leu Ile Ser Asp Phe Lys Asp Pro Pro Thr
                 85                  90                  95

Ala Lys Tyr Arg Ala Ala His Val Phe Phe Thr Asp Ser Cys Pro Asp
            100                 105                 110

Ala Leu Phe Asn Glu Leu Val Lys Ser Arg Ala Ala Lys Val Ile Lys
        115                 120                 125

Thr Leu Thr Glu Ile Asn Ile Ala Phe Leu Pro Tyr Glu Ser Gln Val
    130                 135                 140

Tyr Ser Leu Asp Ser Ala Asp Ser Phe Gln Ser Phe Tyr Ser Pro His
145                 150                 155                 160

Lys Ala Gln Met Lys Asn Pro Ile Leu Glu Arg Leu Ala Glu Gln Ile
                165                 170                 175

Ala Thr Leu Cys Ala Thr Leu Lys Glu Tyr Pro Ala Val Arg Tyr Arg
            180                 185                 190

Gly Glu Tyr Lys Asp Asn Ala Leu Leu Ala Gln Leu Ile Gln Asp Lys
        195                 200                 205

Leu Asp Ala Tyr Lys Ala Asp Pro Thr Met Gly Glu Gly Pro Asp
210                 215                 220

Lys Ala Arg Ser Gln Leu Leu Ile Leu Asp Arg Gly Phe Asp Pro Ser
225                 230                 235                 240

Ser Pro Val Leu His Glu Leu Thr Phe Gln Ala Met Ser Tyr Asp Leu
                245                 250                 255

Leu Pro Ile Glu Asn Asp Val Tyr Lys Tyr Glu Thr Ser Gly Ile Gly
            260                 265                 270

Glu Ala Arg Val Lys Glu Val Leu Leu Asp Glu Asp Asp Asp Leu Trp
        275                 280                 285

Ile Ala Leu Arg His Lys His Ile Ala Glu Val Ser Gln Glu Val Thr
    290                 295                 300

Arg Ser Leu Lys Asp Phe Ser Ser Ser Lys Arg Met Asn Thr Gly Glu
305                 310                 315                 320

Lys Thr Thr Met Arg Asp Leu Ser Gln Met Leu Lys Lys Met Pro Gln
                325                 330                 335

Tyr Gln Lys Glu Leu Ser Lys Tyr Ser Thr His Leu His Leu Ala Glu
            340                 345                 350

Asp Cys Met Lys His Tyr Gln Gly Thr Val Asp Lys Leu Cys Arg Val
        355                 360                 365

Glu Gln Asp Leu Ala Met Gly Thr Asp Ala Glu Gly Glu Lys Ile Lys
    370                 375                 380

Asp Pro Met Arg Ala Ile Val Pro Ile Leu Leu Asp Ala Asn Val Ser
385                 390                 395                 400

Thr Tyr Asp Lys Ile Arg Ile Ile Leu Leu Tyr Ile Phe Leu Lys Asn
                405                 410                 415

Gly Ile Thr Glu Glu Asn Leu Asn Lys Leu Ile Gln His Ala Gln Ile
            420                 425                 430

Pro Pro Glu Asp Ser Glu Ile Ile Thr Asn Met Ala His Leu Gly Val
        435                 440                 445

Pro Ile Val Thr Asp Ser Thr Leu Arg Arg Arg Ser Lys Pro Glu Arg
    450                 455                 460

Lys Glu Arg Ile Ser Glu Gln Thr Tyr Gln Leu Ser Arg Trp Thr Pro
465                 470                 475                 480

Ile Ile Lys Asp Ile Met Glu Asp Thr Ile Glu Asp Lys Leu Asp Thr
```

```
                  485               490               495
Lys His Tyr Pro Tyr Ile Ser Thr Arg Ser Ser Ala Ser Phe Ser Thr
                500               505               510

Thr Ala Val Ser Ala Arg Tyr Gly His Trp His Lys Asn Lys Ala Pro
            515               520               525

Gly Glu Tyr Arg Ser Gly Pro Arg Leu Ile Ile Phe Ile Leu Gly Gly
        530               535               540

Val Ser Leu Asn Glu Met Arg Cys Ala Tyr Glu Val Thr Gln Ala Asn
545               550               555               560

Gly Lys Trp Glu Val Leu Ile Gly Ser Thr His Ile Leu Thr Pro Gln
                565               570               575

Lys Leu Leu Asp Thr Leu Lys Lys Leu Asn Lys Thr Asp Glu Glu Ile
                580               585               590

Ser Ser
```

<210> SEQ ID NO 5
<211> LENGTH: 3754
<212> TYPE: DNA
<213> ORGANISM: Mus musculus

<400> SEQUENCE: 5

```
gcgctgacag cggccggtgc gcgttgtctc cactgtgccc tgcatcccgc atctcgcatc      60
ggccaggcta cccgactcat cgcaaacgtc agtgctcacc atggggaagc ccacgagctc     120
gggatgtgac tggcgccgct tcctacggaa tcactggctg ctgctctcca ccgtggccgc     180
cgtggtacta ggaattgtct taggagtcgt ggttcgagga cacagtgagc tctcaaatct     240
ggataaattc tactttgctt ttcctgggga aattctgatg aggatgctga agctggtcat     300
tttgccgctg atcgtatcca gcatgatcac aggtgtcgct gcactggatt ccaatgtgtc     360
tgggaagatt ggtctgcgcg ctgtagtata ttatttctcc accaccgtca ttgctgtaat     420
cctaggtatt gtgttagttg tgagtatcaa gcctggtgtc actcagaaag tgaatgacat     480
caacaggacg ggtaaaaccc tgaagtcag caccatggat gccatgttgg acctgatcag     540
gaacatgttc cctgagaatc tggtccaagc ctgttttcag cagtacaaaa ccaagcggga     600
agaggtgaag cctgtgggcg atcctggggg gaacgcaacg gaggtgtctg tcaccacagc     660
catgacaaca atgtctgaga acaagacaaa ggaatacaag atcgtgggcc tgtactcaga     720
cggcatcaat gtcctgggct tgattatctt ctgcctcgtc tttggccttg tcattgggaa     780
aatgggagaa aaggggcaga ttctggtgga cttcttcaat gccttgagtg acgccaccat     840
gaaaatcgtc cagatcatca tgtgctacat gccgattggc attttgttcc taattgctgg     900
gaagatcata gaagttgaag actgggaaat attccgcaag ctgggccttt acatggccac     960
tgtcctgagc gggcttgcaa tccactccct catagttctg cccctgctct atttcatagt    1020
tgtgcggaag aacccctttcc gctttgcctt gggtatggcg caggctctcc tgacagctct    1080
catgatctcg tccagttcgg caaccctgcc agttacattc cgctgtgcgg aagaaaagaa    1140
ccaggtagac aagaggatca cgagatttgt gctgcctgtt ggtgccacca tcaacatgga    1200
cggcactgcg ctctacgaag ctgtggcagc cgtgtttatt gcgcaactga atggcttgga    1260
cctaagcatt gggcagatcg tcaccatcag cattacagcc accgctgcca gcattggagc    1320
tgctggggtg cccccaggctg gcctggtgac catggtgatc gtgctgagtg ctgtggggct    1380
gcctgccgag gacgtcaccc tgatcattgc tgttgactgg ctcctggacc ggttcaggac    1440
catggtgaac gtcctgggtg atgcgtttgg gacgggcatc gtagagaagc tctcgaagaa    1500
```

```
ggagctggag cagatggatg tttcgtctga agtcaacatc gtgaacccct ttgccctgga   1560
acccacaacc ctcgataacg aagactcaga taccaagaag tcttatgtca atggggctt    1620 cgcggtagac aaatctgaca ccatctcgtt cactcagacc tcacagttct agatgcctga   1680
cctcagattg aggcctggga ttgtgaaggg cgtctccaca ggagccatct cctagcaaac   1740
tccgacatta aggaacgaga aggacactaa gagtcaactg tacatttagt ttgataaaca   1800
gacctccaga ttattttcta tatttgactt tatagccttg gttctctggg tttagggatt   1860
tggggtgaga tgaactgaaa ggaaattaag aaagttgtgt tatctggatt ttctaattct   1920
atacaacaga gtttggaagt atatgaagta gtaactgtta ggattaggtc atagatatgg   1980
aagagaaatt ggtttctcat gcatagacca gtgtttgggg ttttttaaaca atattattgg  2040 ctacaaattt ttactcaggc tttctattgg caggacttcc tttgccttt tacttttata    2100 gattataatg catctcaaaa gccctaccca gttaatgtgc caaattttcc attttgacct   2160
catctccagc cactctcaaa ctaccctggg gcgggggggag caaaaagat cagcatagtt   2220 ctgcaataac agtttaaaga tagttgtggg gtttagggga agggaagggg tttttttatt   2280
caatgtactg tattgagaca ctggtagctg acagccagtg ttcggtatag aactatatgt   2340
atatgtgtgt atatttatta ttttcatgta atttgcaaga cagagatcag taatgaacta   2400
tcaatgtgaa atacgcagct tcccttgtac ttgaatcaaa acgatagctc cagcctaggt   2460
gtgagctcac cagaacactg tcaggcactc tgggatgaga aatcaagttg ctggcttact   2520
gtgattcaag ccctaaagca gaaacatatt atggtgaaac tctaagatga cacagccatt   2580
cacgtacaac atctagggtc aggctcccgg gaggggggagg ctccctgcga gcatggaata   2640
agtacattta caaaggcact gtagaggcag gaagtgctcc catagcaaca aaaggcttcg   2700
atcttcaagt agacttcaag acccacttca caaggctgtc acttttctgt tcttggtttt   2760
ctctgcctgc gccccccacc cccagggcca aaccagcagt gacaagccac tgctgtttca   2820
aaacggggtg gcctaaattg aataagcctc attgcaaggt gaccaagcta tccttatact   2880
gtcgtctttt tattttatct tctggttttt ttatttttta gttttgaga cagcgcctct   2940 ctacatagcc ctggatatcc tggaactcac tatgtagact agactggcct caaactcaca   3000
gagatcctcc tgcctctgcc tctttagtgc tggcctgaaa ggtaggtacc accatgccca   3060
gctctacact gtatttttac agaagaaaag ccaggccata agcgactggt accagcggtt   3120
cagggacaat acttcagtcc ttccctggag aggattgttc tgggaatctc agccttgtgg   3180
cttagaatcc tctgcctgtc tttctcctgc taattcccga agatggctta taaagtctca   3240
cacttctgtc ctcatcctgt aaataaaact caacaaaaac ttgttcttaa cttggagaca   3300
ggttcataac agccgtgttt ctgtagtgcc cttaagtcat cttaaacccg tgcttttata   3360
tttaagaagc cagaaatcgt gccaaagata gcaggaaggt aaccgaatgc tcagagttgg   3420
ccacgcccac ctgaaagcta ccgactgacc gtcacggtga cccttgactc cgaactttga   3480
agtacaaata tctgtattct ttataggaag taaatctaaa tctaaatgag gttgaatgga   3540
tattttattt aggagtggat ggttctgtcc ccttatcagg tggttctcct tagtggcagt   3600
gaattggcag agccgttcac aagatcattg gggtcatctt gtaaccagcc acttcacaca   3660
ctgtgctgtt aactcaagat gatatgttcc acttccttct caataaacat ctcccccact   3720
cttcctcccc ttaaaaaaaa aaaaaaaaaa aaaa                               3754
```

<210> SEQ ID NO 6

<211> LENGTH: 2849
<212> TYPE: DNA
<213> ORGANISM: Mus musculus

<400> SEQUENCE: 6

| | | | | | |
|---|---|---|---|---|---|
| tagtccaacc | agagacagag | cacactcacc | attttcagag | agagggaagg | ggctcaacct | 60 |
| atgaagagaa | acaaaacaa | acaatgaca | acacagtcc | tctttggatt | cttctccctt | 120 |
| tttatttgta | gtaatgaggg | atgaacctac | agctcggtgc | atactagaaa | aaaacctacc | 180 |
| ctggagctat | atccataccc | attttctttt | tgttttgaaa | cagagtctca | ctaagttatc | 240 |
| caaacagttc | tgaatttgca | atcctcctgc | ctctatctgc | caaggagctg | ggggatagaa | 300 |
| acttgcttgc | accgctgtgt | tgcgctgtct | ttggaggttt | aatcaaataa | ataaaaatat | 360 |
| atagccagct | aatgtgtgtt | gagtatggat | tgcctgtgat | ggaggaataa | gcacgctact | 420 |
| atttcattct | gacagccttt | attcctgcag | ttctgagaag | ttggaaggag | aaagttcact | 480 |
| gaagttgtca | atgctcacag | atttctctaa | caggcgctgg | gctctgtgtt | ctctccccac | 540 |
| caaggcttat | ttacccacac | tgatgcctta | agcttcggga | attcctccac | gccctctgat | 600 |
| ttcctgtaac | tgaatagagg | cctggcaagg | ctctatttag | cactcacctc | aaggtctcag | 660 |
| agttgagtat | ttcctgcact | gtaggccctt | agaagacaga | gcaaggcaag | catttcccct | 720 |
| ttgtgactcc | ccactgtgcc | ttaccagcat | taggaaggcc | ttagaatacc | tgctagcagg | 780 |
| gtactaagca | gtctcaacat | ttttctccca | ttttatctat | tcagaggcaa | ccacaatgat | 840 |
| caatgacaac | aggacctgag | atcaacagca | gcaggtgttt | attttaaaag | tatagaaaac | 900 |
| aggtaaaaac | actgtaaaca | tcaaccagaa | aaattaagga | ctctgctagc | tatttggttt | 960 |
| gtttgtttgt | ttgtttgttt | gtttgttttt | gtaataatgg | ggtctgcaca | caggaccaat | 1020 |
| gctgctccat | gctaggcaag | tttgatcact | gaactctatt | tctagcactc | ttctcgcttt | 1080 |
| ttatgttgag | ccacaatctt | accaacttgc | tccggctggc | cttgaactca | ctttgtaatc | 1140 |
| cctacaagcc | ctgaacttaa | aattctcctg | tcttggtctc | cggaataggt | ctgcctcacc | 1200 |
| atgccagttt | gtattattac | tgataacagt | aaaatctgta | aatgctgcat | atactaaaca | 1260 |
| cttcccaaac | atccctcatt | tagcctctgt | ggcagatttt | ctactaaccc | cggtttacct | 1320 |
| aagaatcaag | gaaggctggg | ggaagttaag | acattcctcc | actggcctgg | agagatgact | 1380 |
| cagaggttaa | gagcatttgc | tgtcctttca | gaggacccag | attcaagtcc | cagttcccac | 1440 |
| gtggcagctt | agaatcatct | gtaactccag | ttccaagagc | tctggcaccc | tcttctgacc | 1500 |
| tcagcaggca | caaagcatgc | gggtacagca | catacacaat | gcaggcaaga | cattcattca | 1560 |
| caataaatta | gttttgtttt | gattttttag | gaactacttt | tctccaaagt | aaattgctgg | 1620 |
| agtccattgc | caggctatcc | taaacaccag | tggcagaaga | cattttcata | agcccccaa | 1680 |
| tgatttcctc | aactgccttt | ctaatcagct | aaacaactaa | gtctgacttc | gcctcaagta | 1740 |
| tattttacta | ctcttttgttt | tagggtaagt | tggtggtctt | agtagagcac | tttgagtttg | 1800 |
| gttaaaaatt | aacagttgca | aatttagaaa | cactgttacc | ttaggcactg | ccatcttaga | 1860 |
| agcctaggag | tcagggggat | cctggacacc | acaagaaaac | aacccacagc | atcaactaag | 1920 |
| cagggctcat | aggcgctcac | agaaactgaa | gcggctagca | cagggcctac | gtgtgtctgt | 1980 |
| gctaggttct | ctgtgtatgt | gttatggttg | tgtagcttgg | tggtcttgta | gaagttgttt | 2040 |
| tcttaggtaa | atgttatttg | tttaatattg | gaataaaact | aagaaaccctt | tctggcctgg | 2100 |
| gaagccatgt | ttctgcccag | gaacacagag | cacctccagc | agctgtctgc | tttgaagctg | 2160 |
| ctaagagctc | gctcaggaag | aagtgaagtc | atccgcttct | atctatcttc | tatctataac | 2220 |

```
gatggcacaa cggttcagta attttgccac aggacagcag aaatgaaggg cgaagaaaaa    2280
ggcgagctgg caatcacttt atttcagttc acttcagtca aacccttgct cccattttt     2340 tttttctag tgtgatttca cacaaagtga ctcatgaaaa ttgcacgcat atgtggggag     2400
attagcaata ccggacttca gtgacactga ggccggcttc cattccattc cacttatatt   2460
gacagctgaa cagctgcttt tttttttttt tttttttttt tttttttttt tttttctcc     2520 cttcagggca aagaacacac acaagcgatg tgtttaaaaa gagatggttt gtatttaaac   2580
tgccagagag aactgacacc acctttagtt taggtagggg atttccgcta gttactttt    2640 gtcctaacat tggataaagc ccactgctct gagtcactaa ccacttccag ccaatcacag   2700 acagccaac acaccgccc gcagccaatt ttctgagccc tgccgtgctt taaccgcaga     2760
accaatccga aggacccgct gtcatctttc atccagctgg ttgtcgctgc cgccgcctcc   2820
agattccgaa ggcgaagctc gcgaagcag                                      2849

<210> SEQ ID NO 7
<211> LENGTH: 37
<212> TYPE: DNA
<213> ORGANISM: Artificial sequence
<220> FEATURE:
<223> OTHER INFORMATION: Synthetic sequence: Primer

<400> SEQUENCE: 7
ttgtcgactt cgcgagcttc gccttcggaa tctggag                             37

<210> SEQ ID NO 8
<211> LENGTH: 36
<212> TYPE: DNA
<213> ORGANISM: Artificial sequence
<220> FEATURE:
<223> OTHER INFORMATION: Synthetic sequence: Primer

<400> SEQUENCE: 8
ttggtaccat agtccaacca gagacagagc acactc                              36
```